(12) United States Patent
Colthurst

(10) Patent No.: US 8,812,119 B2
(45) Date of Patent: Aug. 19, 2014

(54) PLURALITY OF ELECTRONS FOR USE IN THE RESTORATION OF A PATIENT'S HEALTH

(76) Inventor: James Colthurst, Berks (GB)

( * ) Notice: Subject to any disclaimer, the term of this patent is extended or adjusted under 35 U.S.C. 154(b) by 601 days.

(21) Appl. No.: 12/991,024

(22) PCT Filed: May 11, 2009

(86) PCT No.: PCT/EP2009/003331
§ 371 (c)(1),
(2), (4) Date: Feb. 7, 2011

(87) PCT Pub. No.: WO2009/135693
PCT Pub. Date: Nov. 12, 2009

(65) Prior Publication Data
US 2011/0152975 A1     Jun. 23, 2011

Related U.S. Application Data

(60) Provisional application No. 61/051,792, filed on May 9, 2008.

(30) Foreign Application Priority Data

May 9, 2008   (EP) .................................... 08008757

(51) Int. Cl.
*A61N 1/32* (2006.01)
(52) U.S. Cl.
CPC ........................................ *A61N 1/32* (2013.01)
USPC ........................................................ 607/50
(58) Field of Classification Search
CPC ................................................ A61N 1/36071
USPC ............................................ 607/2, 46, 50–51
See application file for complete search history.

(56) References Cited

U.S. PATENT DOCUMENTS

| 6,302,874 B1 | 10/2001 | Zhang et al. | |
|---|---|---|---|
| 2007/0129759 A1 * | 6/2007 | Colthurst | 607/2 |
| 2007/0276449 A1 * | 11/2007 | Gunter et al. | 607/46 |

FOREIGN PATENT DOCUMENTS

| WO | WO 00/02620 | | 1/2000 |
|---|---|---|---|
| WO | WO 2005/118061 | | 12/2005 |
| WO | WO 2005118061 A1 * | | 12/2005 |
| WO | WO 2008/075250 | | 6/2008 |

OTHER PUBLICATIONS

Colthurst, J. et al. "A Retrospective Case Note Review of the Fenzian Electrostimulation System: A Novel Non-Invasive, Non-Pharmacological Treatment," *The Pain Clinic*, 2007, vol. 19, No. 1, p. 7-14.

\* cited by examiner

*Primary Examiner* — Amanda Patton
(74) *Attorney, Agent, or Firm* — Saliwanchik, Lloyd & Eisenschenk

(57) ABSTRACT

Embodiments of the present invention relate to a non-invasive stimulatory adjustment of the body's own self-repair-system using a plurality of electrons. In particular, embodiments of the present invention relate to a plurality of electrons for use in the restoration of a patient's health, preferably a human patient's health in a number of medical conditions. Moreover, embodiments of the present invention relate to a method of treatment using a plurality of electrons for use in the restoration of a patient's health, preferably a human patient's health. Moreover, embodiments of the present invention relate to a method of stimulatory adjustment of the body's own self-repair system using a plurality of electrons.

5 Claims, 17 Drawing Sheets

2nd Stage of General Zone Treatment - 6 Points On Face

2 - 3 'strokes' of device at each point.
As described in training.

Respiratory - Zones for Treatment
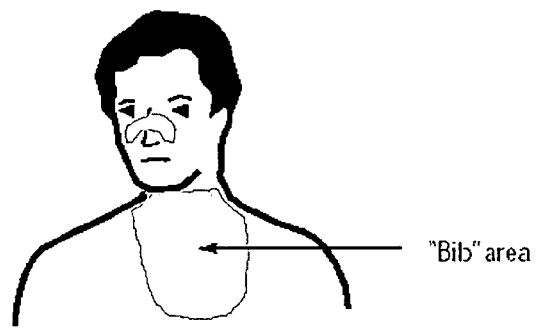
"Bib" area
Back
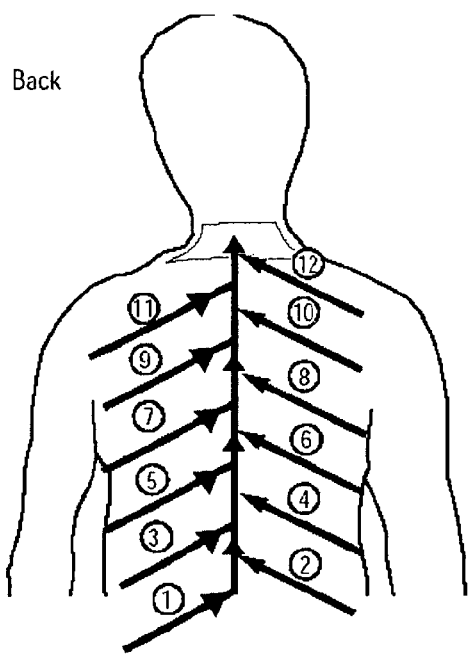
Fig. 4

Gastrointestinal- Main Areas for Treatment
Front
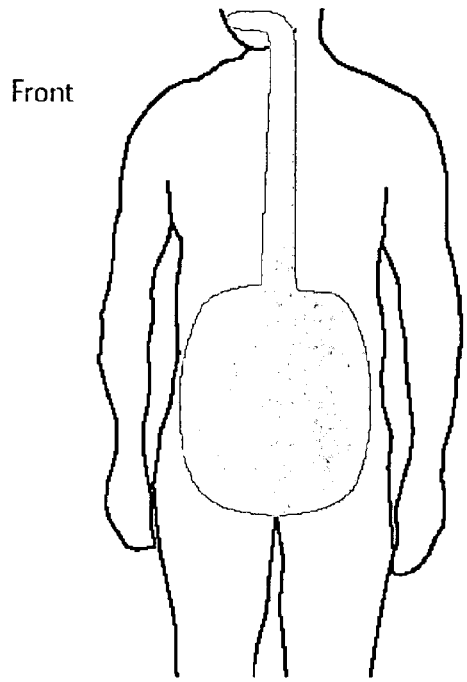
Back
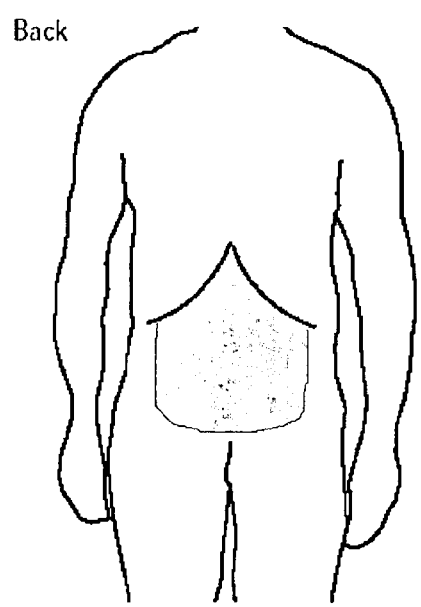
Fig. 6

Kidney/Genito - Urinary Treatment Areas
Back
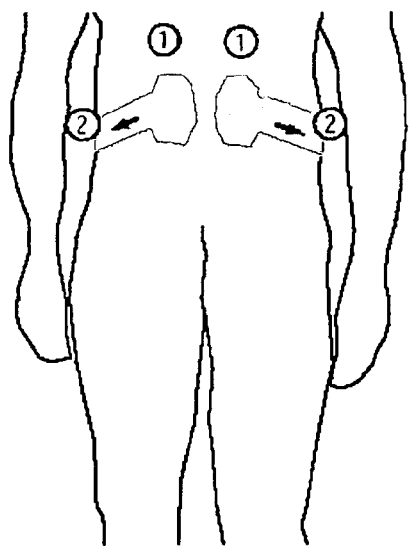
Front
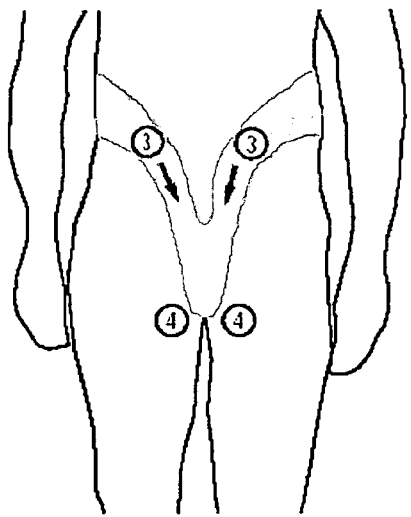
Fig. 8

2nd Stage of General Zone Treatment - 6 points
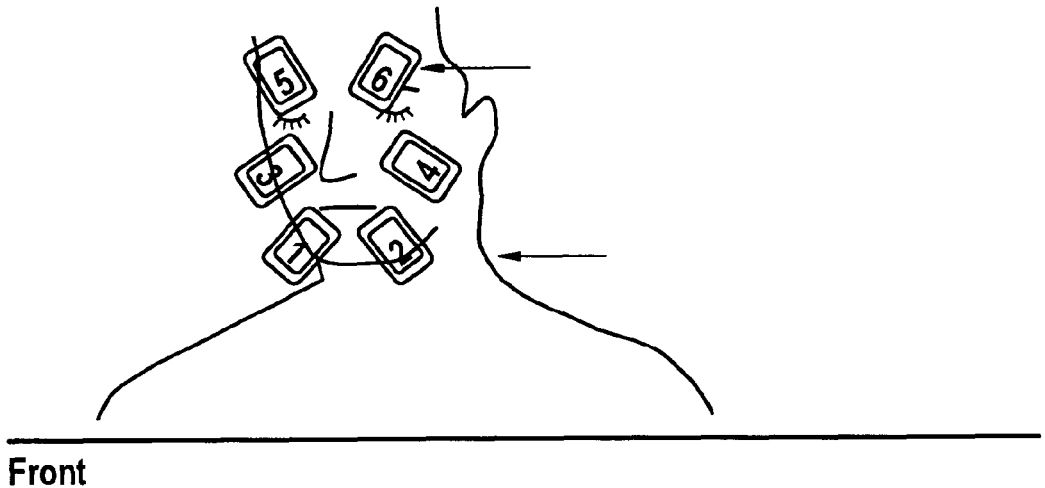
Front
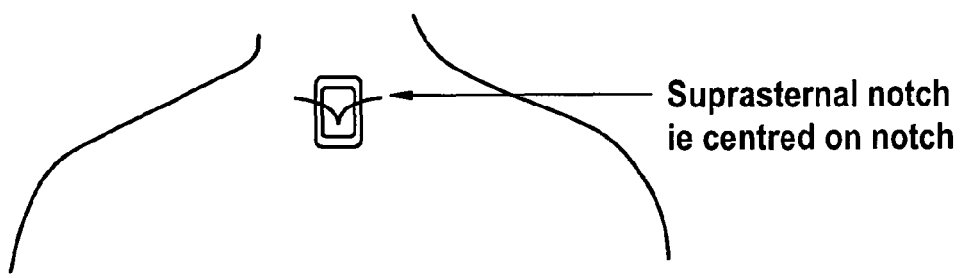
← Suprasternal notch ie centred on notch
Then Back
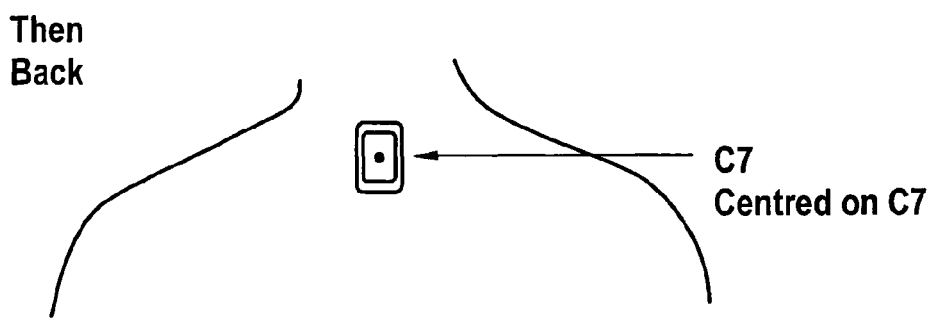
← C7 Centred on C7
Fig. 9b Forehead and Adrenals
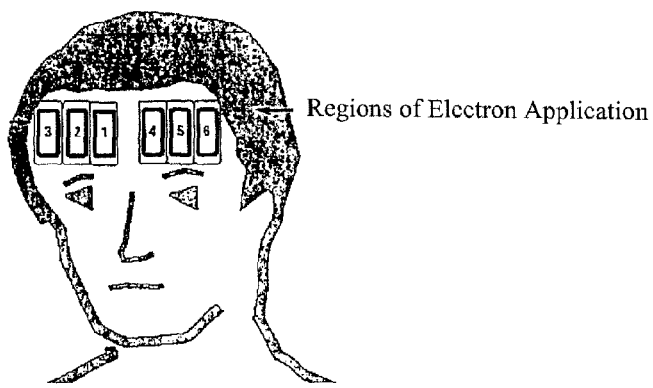
Then
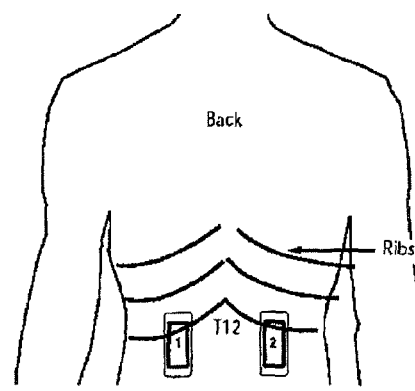
Fig. 11

PLURALITY OF ELECTRONS FOR USE IN THE RESTORATION OF A PATIENT'S HEALTH

CROSS REFERENCE TO A RELATED APPLICATION

This application is a National Stage Application of International Application Number PCT/EP2009/003331, filed May 11, 2009; which claims priority to European Patent 08008757.0, filed May 9, 2008; and also claims the benefit of U.S. Provisional Application 61/051,792, filed May 9, 2008; all of which are incorporated herein by reference in their entirety.

TECHNICAL FIELD

Embodiments of the present invention relate to a non-invasive stimulatory adjustment of the body's own self-repair-system using a plurality of electrons. In particular, embodiments of the present invention relate to a plurality of electrons for use in the restoration of a patient's health, preferably a human patient's health in a number of medical conditions.

BACKGROUND OF THE INVENTION

The development of new drugs for pharmacological treatment is expensive. The same applies to modern medical apparatus technology which, on a global scale only a few health systems in the world can still afford. Accordingly, there is need for treatment facilities of medical conditions which are cheap, affordable, versatile and safe. There also a need for treatment facilities which do not incur side effects, which can be adapted to the individual patient and which can be applied without the risk of major side effects.

There are a number of therapies involving the use of electrical currents, such as electro-convulsive therapy (ECT), transcutaneous nerve stimulation (TENS), vagus nerve stimulation (VNS), deep brain stimulation (DBS), transcranial direct current stimulation (tDCS), transcranial magnetic stimulation (TMS) and magnetic seizure therapy (MST). Some of them are fairly drastic in effect; they have a very specific focus, and all of them are experimental.

WO20005/118061 describes a device for applying electrical impulses to the skin of a patient. Specific medical indications are not disclosed.

SUMMARY OF THE INVENTION

Embodiments of the present invention involve the application of a plurality of electrons for use in the restoration of a patient's health, preferably a human patient's health, wherein said plurality of electrons is applied to said patient as a series of alternating current (AC) signals of a duration of approximately 5 to 100 μs and an amplitude of approximately 10 V to 100 V using a device having electrodes, said AC signals being applied to the body (e.g., skin) of said patient at several sites, such as at the back and/or chest and/or neck and/or face of said patient, and, optionally, at one or more sites suspected of being in a pathological state, wherein said restoration of a patient's health, preferably a human patient's health, is an alleviation or cure of a disease selected from diseases of the respiratory system, diseases of the cardiovascular system, diseases of the gastroenterological system, skin diseases, muscular-skeletal diseases, neurological diseases, ophthalmological diseases, genito-urinary diseases and inflammatory diseases.

In one embodiment, the patient is a mammal. In one particular embodiment, the patient is a human patient.

Diseases of the respiratory system include, but are not limited to asthma, respiratory allergy, pneumonia, bronchitis, rhinitis, sinusitis, tracheitis, pharyngitis, croup, and otitis.

Diseases of the cardiovascular system include, but are not limited to angina pectoris, ischemic myocardial infarction, arrhythmia, post-myocardial infarction pain, myocarditis, heart failure, and hypertension.

Diseases of the gastroenterological system include, but are not limited to stomach ulcers, gastritis, liver cirrhosis, pathological states of the oesophagus, gallstones, pancreatitis, constipation, diarrhea, hemorrhoids, and fistulae or inflammation of the rectum.

Skin diseases include, but are not limited to psoriasis, neurodermatitis, dermatitis, atopic dermatitis.

Muscular-skeletal diseases include, but are not limited to back pain, lumbago, fractures, pulled muscle, torn ligament or tendon, disc prolapse, ischiatitis, osteoporosis, Perthes disease, osteoarthritis, gout, muscle cramp, diseases affecting the integrity of joints, such as age-related disintegration of joints.

Neurological diseases include, but are not limited to Alzheimer, Parkinson, multiple sclerosis, dementia, neuralgias, and stroke.

Ophthalmological diseases include, but are not limited to glaucoma, retinopathy, retinal macula degeneration, eye infections, and retinal detachment.

Genito-urinary diseases include, but are not limited to male genital conditions selected from prostatism, impotence, infertility, testicular disease, female conditions selected from pre/postmenstrual pains, fibroids, endometriosis, infertility, myoma, fibromyoma, inflammatory pelvic conditions, diseases of the ovaries, oviduct(s) or cervix, and menopause.

Inflammatory diseases include, but are not limited to chronic and acute inflammatory diseases, said chronic inflammatory disease being selected from rheumatoid arthritis, chronic obstructive pulmonary disease, asthma, angina pectoris, osteo-arthritis, inflammatory bowel diseases such as Crohn's disease or ulcerative colitis, psoriasis, multiple sclerosis, systemic lupus erythematosus and artherosclerosis, said acute inflammatory disease being selected from pathogenic states involving an immune response in an injured tissue to an injurious agent which immune response serves to destroy, dilute or isolate said injurious agent and the injured tissue, said acute inflammatory disease being selected from inflammation of the skin, inflammation of internal organs, such as colitis, gastroenteritis, pneumonia, infective illnesses such as wound infections, tuberculosis, influenza, sinusitis, chest infections, such as bronchitis, allergies such as hay fever, and hemorrhoids, Further examples of inflammatory diseases, i.e. diseases having an inflammation component and being amenable to treatment using a plurality of electrons, in accordance with the present invention, are shown in FIG. 13.

In one embodiment said AC signals are applied at said several sites by placing the electrodes of said device on the skin at the respective site, whilst impedance of said skin and the rate of change of said impedance at the respective site is measured, and wherein from said several sites, one site or a subset of sites is selected for further or repeated application of AC signals, said one site or subset of sites being selected for initially, at a first application of said AC signals, having the highest rate of change of skin impedance or having a maximum of skin impedance in comparison to other sites or having a skin impedance higher than adjacent sites.

In another embodiment said AC signals are applied at said several sites by sliding the electrodes of said device over the skin at the respective site, whilst monitoring changes in friction of the skin against said device, changes of sensation of the patient, changes in color of the skin and/or a combination of the foregoing, and wherein, from said several sites, one site or a subset of sites is selected for further or repeated application of AC signals, said one site or subset of sites being selected for initially, at a first application of said AC signals, exhibiting a change of friction of the skin against said device, a change of sensation of the patient, a change of color of the skin and/or a combination of the foregoing.

In one embodiment, at said selected one site or said selected subset of sites, further AC signals are applied for a period of time from 30 s to 5 min and, optionally, until the rate of change of skin impedance is zero.

It should be noted, that the plurality of electrons is applied to said patient as series of AC signals, wherein said plurality of electrons acts as a pharmacologically active substance. In one embodiment, during application of said AC-signals, no chemical substance other than said plurality of electrons is applied to said patient. Moreover, in one embodiment, the application of said plurality of electrons as a series of AC signals is not used to deliver a chemical composition or agent to the patient, other than the plurality of electrons itself. The plurality of electrons are not used for iontophoretical application of an agent to a patient or for application of an agent through electroporation. Moreover, the plurality of electrons are not used for delivery of substances or agents or compositions to the patient, other than the electrons themselves. In one embodiment, the plurality of electrons are applied as a series of AC-signals, as defined further above, without additional substances or additional agents or additional compositions being applied through iontophoresis or electroporation.

In one embodiment said restoration of a patient's health, preferably a human patient's health, may provide an alleviation or cure of a disease of the respiratory system, wherein said disease of the respiratory system is selected from asthma, respiratory allergy, pneumonia, and bronchitis, and wherein said AC signals are applied to the skin of said patient at the back and the chest of said patient.

In one embodiment said restoration of a patient's health, preferably a human patient's health, may provide an alleviation or cure of a disease of the respiratory system, wherein said disease of the respiratory system is selected from rhinitis, sinusitis, tracheitis, pharyngitis, croup, and otitis, and wherein said AC signals are applied to the skin of said patient at the neck, the nose, the sinuses, around and behind the ear and/or the thoracic spine of the patient.

In one embodiment said restoration of a patient's health, preferably a human patient's health, may provide an alleviation or cure of a disease of the cardiovascular system, wherein said disease of the cardiovascular system is selected from angina pectoris, ischemic myocardial infarction, arrhythmia, post-myocardial infarction pain, myocarditis, heart failure, and hypertension, and wherein said AC signals are applied to the skin of said patient at the back and/or the chest in an area of the skin underneath of which the heart is located, and in an area of skin underneath of which the thoracic spine is located, and on the palms of the hands and the soles of the feet of said patient.

In one embodiment said restoration of a patient's health, preferably a human patient's health, may provide an alleviation or cure of a disease of the gastroenterological system, wherein said disease of the gastroenterological system is selected from stomach ulcers, gastritis, liver cirrhosis, pathological states of the oesophagus, gallstones, pancreatitis, constipation and diarrhea, hemorrhoids, fistulae or inflammation of the rectum, and wherein said AC signals are applied to the skin of said patient on the abdomen, and/or in an area of skin underneath of which the organ or site affected by said disease of the gastroenterological system is located.

In one embodiment said restoration of a patient's health, preferably a human patient's health, may provide an alleviation or cure of a skin disease, wherein said skin disease is selected from psoriasis, neurodermatitis, dermatitis, in particular atopic dermatitis, and wherein said AC signals are applied to the skin in a site of the skin affected by said skin disease, if said skin disease is restricted to an area of body surface of the patient not larger than 10 cm$^2$, and wherein said AC signals are applied to the skin in at least a first site of the skin affected by the skin disease and, additionally, at least a second site of the skin unaffected by the skin disease, if said skin disease affects an area of body surface of the patient larger than 10 cm$^2$.

In one embodiment said restoration of a patient's health, preferably a human patient's health, may provide an alleviation or cure of a disease of the musculo-skeletal system, and wherein said AC signals are applied to the skin of said patient in a position overlying an element of the musculo-skeletal system affected by said musculo-skeletal disease, such as joint, bone, tendon, connective tissue or muscle.

In one embodiment said restoration of a patient's health, preferably a human patient's health, may provide an alleviation or cure of a neurological disease, and wherein said AC signals are applied to the skin of said patient at the back and/or chest and/or face and/or neck and/or skull and/or spine of the patient.

In one embodiment, said neurological disease is stroke, and wherein said AC signals are applied to the skin of said patient on the skull of the patient, amongst other possible areas.

In one embodiment said restoration of a patient's health, preferably a human patient's health, may provide an alleviation or cure of an ophthalmological disease, and wherein said AC signals are applied to the skin of said patient periorbitally, and/or at the neck and/or face and/or over the closed eye(s).

In one embodiment said restoration of a patient's health, preferably a human patient's health, may provide an alleviation or cure of a genito-urinary disease, and wherein said AC signals are applied to the skin of said patient at the neck and shoulders, and in a position overlying the kidney(s), the bladder, the ureters, the liver, the pancreas and/or the spine.

In one embodiment, said genito-urinary disease is a male genital condition selected from prostatism, impotence, infertility and testicular disease, and wherein said AC signals are applied to the skin in regions overlying the ureters, and/or to the skin at the inguinal lymph nodes, the perineum, the scrotum, the penis, and the buttocks, or wherein the genito-urinary disease is a female condition, selected from pre/post-menstrual pains, fibroids, endometriosis, infertility, myoma, fibromyoma, inflammatory pelvic conditions, diseases of the ovaries, oviduct(s) or cervix, and menopause, and wherein the AC signals are applied to the skin of the patient at the abdomen and/or neck and/or lower back.

In one embodiment, said restoration of a patient's health, preferably a human patient's health, is an alleviation or cure of an inflammatory disease, wherein said inflammatory disease is a chronic or acute inflammatory disease, said chronic inflammatory disease being selected from rheumatoid arthritis, chronic obstructive pulmonary disease, asthma, angina pectoris, osteo-arthritis, inflammatory bowel diseases such as Crohn's disease or ulcerative colitis, psoriasis, multiple sclerosis, systemic lupus erythematosus and artherosclerosis, said acute inflammatory disease being selected from pathogenic states involving an immune response in an injured tissue to an injurious agent which immune response serves to destroy, dilute or isolate said injurious agent and the injured tissue, said acute inflammatory disease being selected from inflammation of the skin, inflammation of internal organs, such as colitis, gastroenteritis, pneumonia, infective illnesses such as wound infections, tuberculosis, influenza, sinusitis, chest infections, such as bronchitis, allergies such as hay fever, and hemorrhoids, and wherein said AC signals are applied to the skin of said patient at the back, spine, chest, face and neck of the patient, and/or at the site of inflammation on the skin and/or in an area of skin underneath of which the inflamed organ or tissue is located.

In one embodiment, said inflammatory disease is selected from autoimmune diseases, such as rheumatoid arthritis, systemic lupus erythematosus, inflammatory bowel diseases such as Crohn's disease or ulcerative colitis, infective illnesses, such as wound infections, tuberculosis, influenza, sinusitis, and wherein said AC signals are applied to the skin of said patient at the back, spine, chest, face and neck of the patient, and/or at the site of inflammation on the skin and/or in an area of skin underneath of which the inflamed organ or tissue is located.

In one embodiment at the end of the application of said AC signals, a final series of AC signals is applied which AC signals are frequency modulated having a range of frequencies from 15-351 Hz, preferably over a period of 1 to 20 seconds, more preferably 5-10 seconds, most preferably 8 seconds.

Embodiments of the present invention also relate to a method of treatment using a plurality of electrons for use in the restoration of a patient's health, preferably a human patient's health, wherein said plurality of electrons is applied to said patient as a series of alternating current (AC) signals of a duration of approximately 5 to 100 μs and an amplitude of approximately 10V to 100V using a device having electrodes, said AC signals being applied to the body, e.g. skin of said patient anywhere on the surface of the body, in particular at several sites, such as at the back and/or chest and/or neck and/or face of said patient, and, optionally, at one or more sites suspected of being in a pathological state, wherein said restoration of a patient's health, preferably a human patient's health, is an alleviation or cure of a disease selected from diseases of the respiratory system, diseases of the cardiovascular system, diseases of the gastroenterological system, skin diseases, muscular-skeletal diseases, neurological diseases, ophthalmological diseases, genito-urinary diseases, and inflammatory diseases, wherein said application of said AC signals, said diseases and said sites are as defined above.

Embodiments of the present invention also relate to a method of stimulatory adjustment of the body's own self-repair-system of a patient, preferably a human patient, using a plurality of electrons, wherein said plurality of electrons is applied to said patient as a series of alternating current (AC) signals of a duration of approximately 5 to 100 μs and an amplitude of approximately 10V to 100V using a device having electrodes, said AC signals being applied to the body, e.g. skin of said patient anywhere on the surface of the body, in particular at several sites, such as at the back and/or chest and/or neck and/or face of said patient, and, optionally, at one or more sites suspected of being in a pathological state, wherein said stimulatory adjustment of the body's own self-repair-system is used to cause an alleviation or cure of a disease selected from diseases of the respiratory system, diseases of the cardiovascular system, diseases of the gastroenterological system, skin diseases, muscular-skeletal diseases, neurological diseases, ophthalmological diseases, genito-urinary diseases, and inflammatory diseases, wherein said application of said AC signals, said diseases and said sites are as defined above.

Embodiments of the present invention may provide a new approach to the treatment of pathological states.

It should be noted that the term "skin", as used herein, includes both the type of skin which covers the vast majority of the human body, such as the skin on the legs, arms and the torso of the body, as well as the type of skin characterized by a considerable hair growth, such as the scalp. The term "skin" may also include additional areas as points of entry of treatment, such as the eye(s), the ear(s) and the mouth.

The inventors have surprisingly found that in using specific sites on the body, in particular on the skin as a point of entry, a large variety of medical conditions may be treated. Without wishing to be bound by any theory, embodiments of the present invention assume a "dialogue" of sorts between skin cells and the central nervous system via nerve fibres, in particular unmyelinated c-fibres, most likely due to the common ancestry of skin cells and nerve cells, both being embryologically derived from the neuroectoderm. Embodiments of the present invention assume that the skin can be considered as a "peripheral brain" through which a dialogue with the central nervous system can be initiated. Changes within the body, such as pathology, may result in an altered skin impedance which may occur, for example over the site of the diseased organ, or it may even manifest itself in an apparently unrelated area of the skin. Hence, specific centres in the central nervous system, for example the spine may be addressed through electrical stimulation of the skin using a plurality of electrons as the "pharmacological substance". The body is essentially "initiated" to undergo a process of self-repair and healing, and the plurality of electrons when applied to the correct site initiates the body's self-repair system. In this context, it should be noted that pain and inflammation are the body's "attention seekers" for the body's self-repair-systems (the body's "works departments", so to speak) (see also FIGS. 14 and 15). The present invention, by initiating a dialogue between skin cells and the CNS, leads to an alert of the CNS, which, in turn, causes an allocation of resources of the body's self-repair system. The present invention ensures that this allocation of resources is done in the right, i.e. appropriate way, thus leading to a reduction of pain and inflammation, concomitantly with such repair being initiated and successfully completed.

Again, without wishing to be bound by any theory, the physiological processes underlying the pharmacological effect provided by the plurality of electrons when applied to the skin are believed to be as follows:

Embodiments of the invention depend on a device using alternating current electrostimulation via a biofeedback system based on reaction to skin impedance. The impulses are typically of short duration (5-100 μs, preferably 10 μs approx) and of relatively high amplitude (10V-100V, preferably ca. 80V). The influence is critically controlled by careful observation using specific measured parameters of the impulses depicted on the device screen. Due to the short duration of impulse the energy of the signal is extremely small and harmful effects highly unlikely.

A device suitable to be used in the present invention is an electron producing device. An example of such device has been described in WO2005/118061.

The equipment is able to detect the areas of lowest skin impedance in an "area of possibility" (between two electrodes, e.g., concentric rectangular electrodes) which it denotes by numerical readout. Dialogue is typically initiated through points of the skin having low impedance, where the biofeedback is relatively more active (and so more efficacious), especially when guided by observation of this dialogue by a trained practitioner. The term "biofeedback", as used herein, is generally meant to refer to the responsivity of the skin towards the application of AC signals, as measured for example, by the rate of change of skin impedance. "Biofeedback" is "active" in those sites where the rate of change of skin impedance is higher in comparison to adjacent sites. Other indicators of "biofeedback" include redness of the skin, friction of the skin, skin sensation of the patient and other detectable parameters. Areas in which biofeedback is active are also sometimes herein referred to as areas "where Fenzian is found".

Via nerve endings the afferent impulses from the device enter the central nervous system (CNS) at the anterior horns of the spinal cord. Both myelinated and unmyelinated nerves are stimulated by the impulses. By numerical supremacy the majority of the dialogue takes place via the c-fibres. Impulses are typically conducted up the dorsal and ventral spinothalamic tracts, the dorsal and ventral spinocerebellar tracts and the spinotectal tracts. There may also be a contribution via the reticulo-cerebral fibres and the pontine tegmentum. Some of the facilitatory effects of the electrostimulatory system are believed to be mediated by this part of the reticular formation. Anohin demonstrated continuation of the reticular formation communications beyond brain stem to the cortex with associated influence on cortical responses. Efferent signals typically descend via the corticospinal tracts. Frequently, more than one segmental levels are influenced simultaneously. This may result in 'unexpected' recovery from old pathology whilst treating an apparently unconnected presenting complaint.

Via diverse neurotransmitters, influences alter the signals on foci of dominance relating to both reflex arcs and autonomic regulation with attendant distal influence and alteration of efferent impulses on both the autonomic and peripheral systems. The degree to which these responses are affected is in turn adjusted by the higher cortical and pontine impact on the lability of the lower spinal system. Foci in the spinal cord, possibly present for many years as a result of unresolved or incompletely resolved pathology may be re-stimulated by the electrostimulation so that 'normal' pathways can resume the 'stalled' resolution process. A 'hierarchy of dominance' of these foci prevails in the spinal cord. This hierarchy may relate either to the relative survival advantage of a particular complaint or the historic acquisition of the pathology. Fushpan and Potter (in the 1950s) demonstrated the variability of synaptic response between synapses predominating in chemical stimulation and those predominating in electrical stimulation. Many disorders relate to disturbed chemistry of synaptic transmission. Some of these effects become longstanding 'locked' processes (e.g., Parkinsons). Electrostimulatory activity can help to break chronic cycles to allow previously 'healthy' patterns of synaptic activity to become re-established.

Electrostimulatory influences have small local effects in the form of polarisation of molecules and local vasomotor effects; with some possible influence on the graded potentials locally. Mediation of local influences is via neuropeptide release.

The majority of the beneficial influence is via efferent nerves from the CNS. At a segmental level, there is also sometimes influence on pain pathways via the saturation of transmitter at the site of entry into the lateral spinothalamic tract, particularly if there is marked A fibre involvement.

Electrostimulation signals act on both local reflex arcs (also influencing the sympathetic chain) with their concomitant effects on internal organ, vessels and muscles; as well as entering the CNS via the ascending tracts for higher connections which will lead to general neuropeptide release (with resultant effect on general homeostasis), endocrine release, parasympathetic influence and efferent signals down the corticospinal tracts to the relevant levels. Processes of disease control and pain with this form of electrostimulation are mainly mediated via the descending impulses in the CNS to an appropriate level for subsequent peripheral 'local' neuropeptide release. Further mediation is influenced through the autonomic nervous system both via local effects and general physiology.

The skin impedance alterations, which occur as a result of both the local and general state, may, for example, be depicted numerically on the device and influence the next outgoing signal from the device. In other embodiments, the skin impedance alterations may also be represented by the device through audible or otherwise detectable signals, or both audible and visual signals. Moreover, several other aspects of the signal exchange between the skin and the device may be depicted numerically on the screen of the device (amplitude, rate, gradient, speed and so on) or may be represented by audible or other detectable signals. Some of these numbers use mathematical algorithms to be able to generate the best possible use of the electrostimulatory dialogue. The numerical or other representations are used by the practitioner to guide the treatment processes, via a number of protocols. The intention is to guide the locked or disturbed CNS foci into a restorative state; thereby initiating or re-stimulating normal repair processes; both centrally and locally. Due to the strong CNS (vs. local) component of the process of exchange, 'old' foci from previous pathological states can be influenced simultaneously, leading to unexpected final resolution of past disease states.

At the end of several treatment processes, a protocol of 'frequency modulation' can be selected. In this process, the device output signal can be asked to cycle through a range of frequencies, e.g., from 15-351 Hz in an 8 second cycle. The primary value of this process is believed to be based on the fact that the 'end' of a biofeedback treatment at a specific point on the skin leads to a prolongation of the wave pulse as part of a specific communication loop via either a reflex arc or a spino-cerebral path. This 'dominant' communication is the more significant part of the healing stimulus. But there are other associated communication paths which are accessory to the focal process, or are linked to previous pathology, which are affected by the dominant process. These accessory pathways may function at different frequencies and cannot simultaneously be addressed by the major waveform during the biofeedback process. Again, without wishing to be bound by any theory, it is believed that by cycling through the frequency range these other accessory networks are reached.

A device suitable to be used in the present invention has, for example, been described in WO 2005/118061. Such device comprises, for example, a pair of electrodes for contact with the skin; a waveform generator for repeatedly generating an AC waveform for applying electrical impulses through the electrodes to the skin; a detector for detecting changes in the skin impedance and for generating output signals representing a skin impedance; means responsive to the output signals from the detector for monitoring the responsivity of the skin; and indicator means for generating a first indication when a predetermined level of responsivity is reached and a second indication when a predetermined treatment has been administered. In this device, the skin impedance alterations which occur as a result of changes both in the local and the general state are depicted numerically on a screen of the device and influence the next outgoing signal from the device. Moreover, several other aspects of the signal exchange between the skin and the treatment device may be depicted numerically on the screen, such as the amplitude, the rate, the gradient, the speed etc. Some of these numbers use mathematical algorithms to be able to generate the best possible use of the electro stimulatory dialog. The numerical representations may then be used by the practitioner to guide the treatment processes via a number of protocols. The intention is to guide the locked or disturbed centres within the central nervous system, which are herein also sometimes referred to as CNS foci into a restorative state, thereby initiating or re-stimulating normal repair processes, both centrally and locally. Due to the strong CNS (versus local) component of the process of dialog exchange, "old" foci from previous pathological states can be influenced simultaneously, leading also to unexpected resolutions of past disease states.

The device may be embodied in the form of a handheld battery-powered device. Hence, the plurality of electrons are provided from the battery as a reservoir of electrons, and such reservoir of electrons is eventually consumed, and hence, effectively the pharmacological substance is consumed by the body.

In this device, the detection-means generates output signals in the form of pulses whose duration represents the skin impedance; the monitoring means measures the duration t of each pulse; and the indicating means is arranged to generate each indication when t satisfy a predetermined function of t. In one embodiment, which is a preferred embodiment, to which, however, the present invention is not limited, the indicating means is arranged to generate the first indication when $t_2 = 4.087 \, t_1^{0.7131}$ and to generate the second indication when $dZ/bT = 0$, wherein $Z =$ skin impedance. The electrical impulses generated by the handheld device are of high initial amplitude (10V-100V) and brief duration (5 μs-100 μs). The resulting treatment is non-invasive and does not generate harmful side-effects.

Further aspects of the device are outlined in WO 2005/118061 which is incorporated herein in its entirety. Embodiments of the present invention are not limited, however, by the specific device described in the WO 2005/118061 application.

The present invention also relates to a method of treating a living body through the skin, comprising the steps of: placing a pair of electrodes in contact with the skin; generating an AC waveform to supply electrical impulses through the electrodes to the skin of said patient; detecting changes in the skin impedance and generating output signals representing the skin impedance; monitoring the responsivity of the skin; and indicating firstly when a predetermined level of responsivity is reached and secondly when a predetermined treatment has been administered, wherein the diseases benefiting from such treatment and the sites of treatment on the skin are as outlined above.

The present invention also relates to a method of stimulatory adjustment of the body's own self-repair-system of a patient, preferably a human patient, using a plurality of electrons, said method comprising the steps of: placing a pair of electrodes in contact with the skin of said patient; generating an AC waveform to supply electrical impulses through the electrodes to the skin; detecting changes in the skin impedance and generating output signals representing the skin impedance; monitoring the responsivity of the skin; and indicating firstly when a predetermined level of responsivity is reached and secondly when a predetermined treatment has been administered, wherein the diseases benefiting from such treatment and the sites of treatment on the skin are as outlined above.

Such device useful in the practice of the present invention is herein also sometimes referred to as a "Fenzian" device and the corresponding treatment as "Fenzian" treatment.

The inventors have found that a plurality of electrons in accordance with the present invention may be used for treating, i.e., alleviating or curing diseases of the respiratory system, diseases of the cardiovascular system, diseases of the gastro enterological system, skin diseases, musculo-skeletal diseases, neurological diseases, ophthalmological diseases, genito-urinary diseases and inflammatory diseases. When applied to a number of sites on the skin, particularly at the back, and/or the chest, and/or the neck and/or the face and, optionally at one or more sites suspected of being in a pathological state, a plurality of electrons may initiate the body's own repair mechanisms by activating points of synaptic concentration, (also herein sometimes referred to as CNS foci), which in turn may influence the organ/location affected by the disease due to innervation of the organ. Such activation may occur through the release of neuropeptides at the respective innervating nerve endings which, in turn, control self-replacement, structure and behaviour.

In the following, reference is made to the figures, wherein

FIG. 4 shows a schematic representation of one option for the treatment areas for diseases of the respiratory system, according to an embodiment of the invention;

FIG. 6 shows a schematic representation of one example approach to the treatment areas for diseases of the gastroenterological system, according to an embodiment of the invention;

FIG. 8 shows a schematic representation of one example approach the treatment areas for diseases/pathological states effecting the kidneys and/or the urinary tract, according to an embodiment of the invention;

FIGS. 9a-9b shows the first stage (FIG. 9a) and the second stage (9b) of a general zone spinal treatment using one of many possible numerical approaches, wherein values of skin impedance are recorded/measured, according to an embodiment of the invention;

Figure 12:
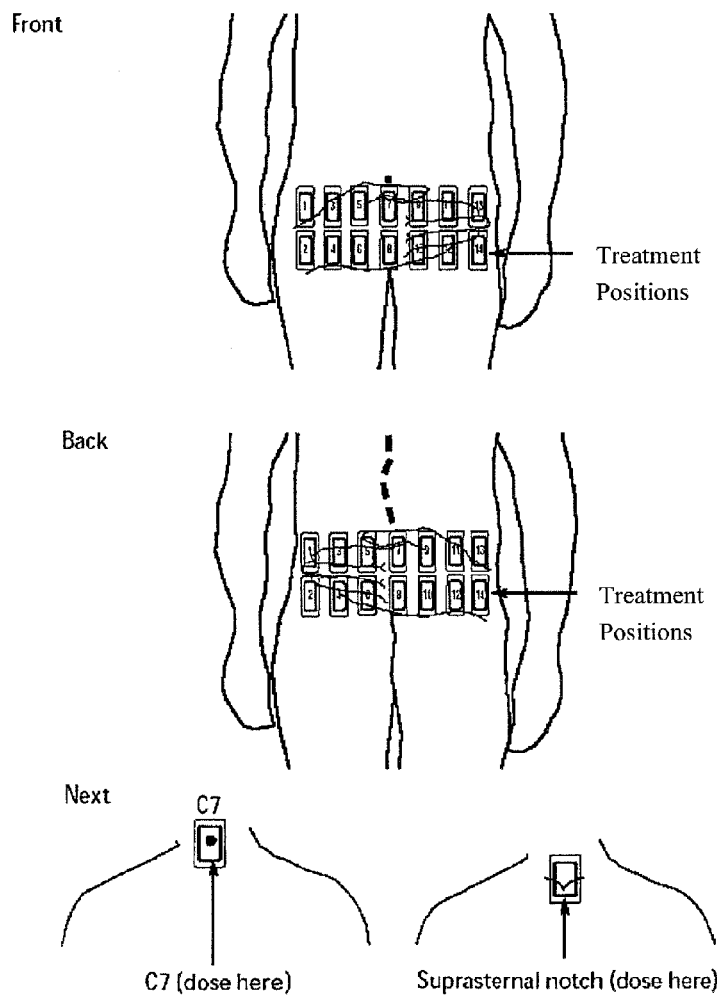

FIG. 11 shows a schematic representation of the part of a general treatment which includes the forehead and adrenals, wherein each numbered position refers to a position where the electrodes of the device are subsequently held, according to an embodiment of the invention; and FIG. 12 shows another embodiment of a numerical treatment method of the pelvis/lower abdomen region, according to an embodiment of the invention.

Figure 13:
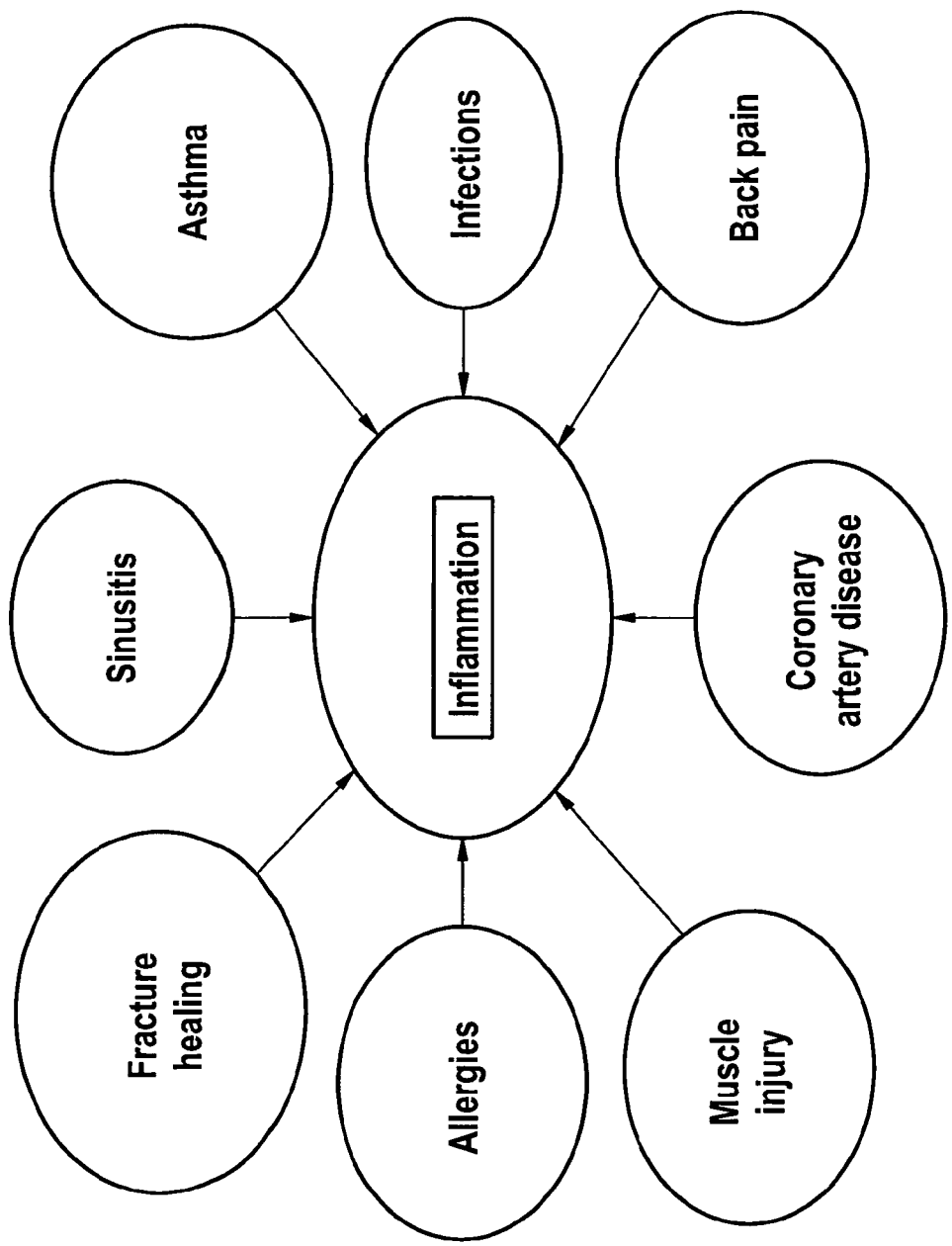

FIG. 13 is a diagram illustrating the involvement of inflammation in a number of exemplary diseases and pathological states, all of which are amenable to treatment using a plurality of electrons, in accordance with the present invention.

Figure 14:
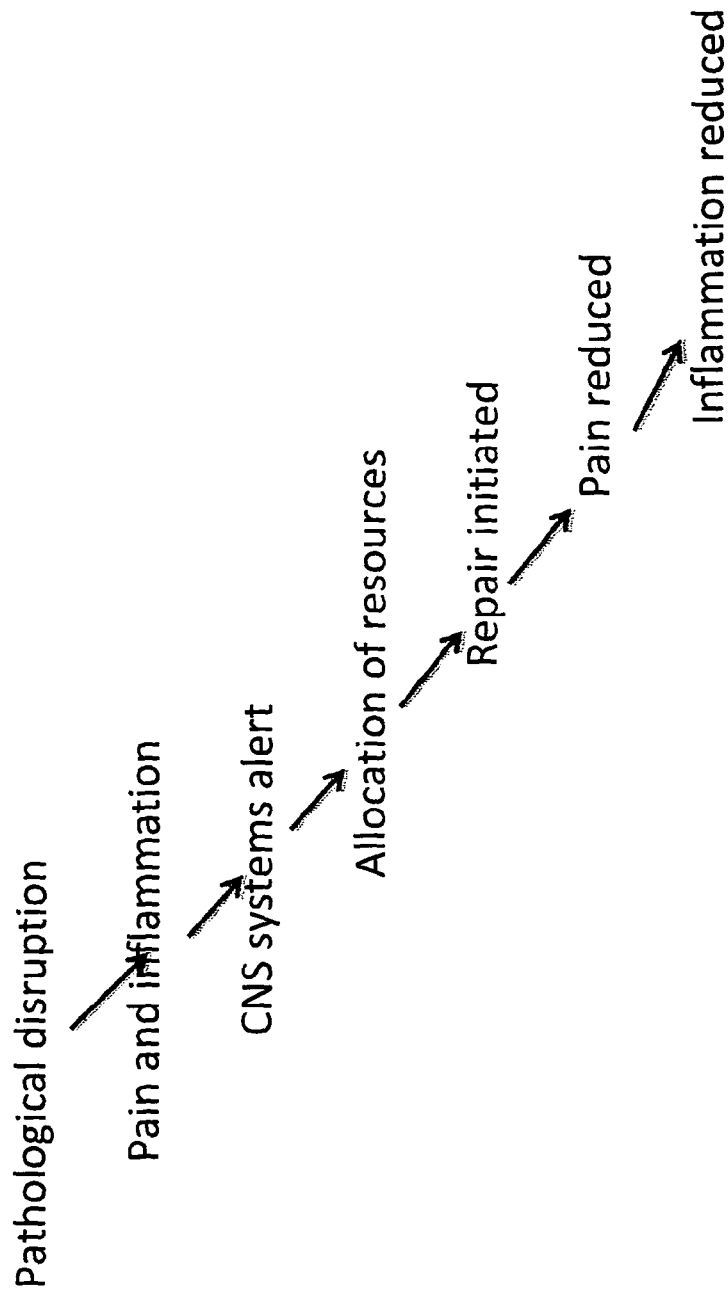
Figure 15:
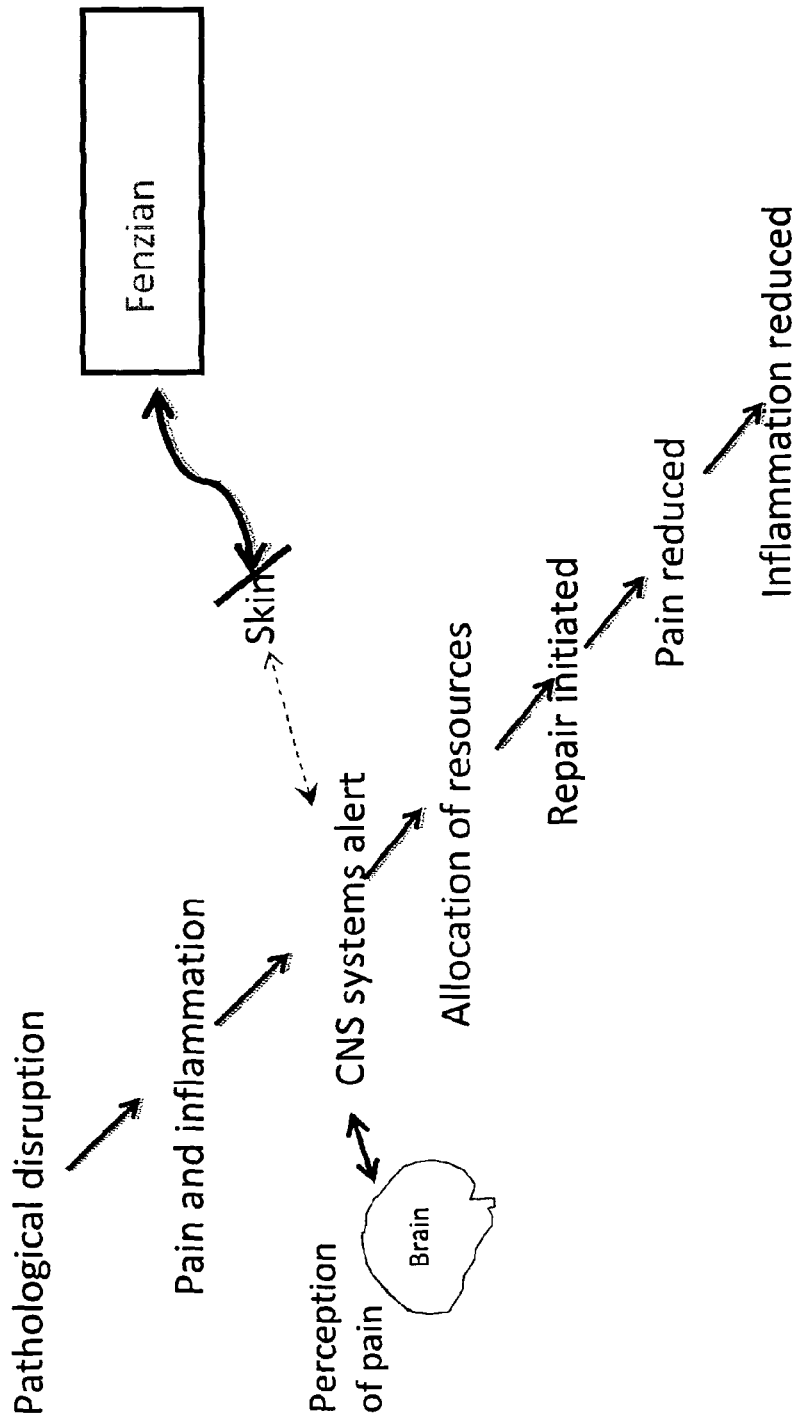

FIGS. 14 and 15 demonstrate a series of events believed to be involved in a pathological process and how treatment in accordance with the present invention using a plurality of electrons, (e.g. using a "Fenzian" device, as outlined above), may influence such series of events by communication with the central nervous system (CNS). More specifically, FIG. 14 illustrates that pain is an "attention-seeker" for the body's own self-repair-system, (the "Works Department", so to speak). The pain and inflammation which follow a pathological disruption, such as an injury, trauma or infection, causes an alert in the central nervous system (CNS) which, in turn, leads to an allocation of resources of the body's self-repair-system. This causes an initiation of repair activities which, upon completion, leads to a reduction of pain and inflammation.

FIG. 14 shows the course of events which are believed to happen typically following a pathological disruption.

FIG. 15 illustrates the stage at which the present invention is believed to interact with this process, namely at the key stage of the alert of the CNS; at this stage, the self-repair resources are being allocated, and the present invention ensures that this allocation of resources is done in the right, i.e. appropriate way.

DETAILED DISCLOSURE OF AN EMBODIMENT OF THE INVENTION

Furthermore, in the following, by way of example, a number of treatment regimens are described, wherein electrons are applied to the skin of the patient. It should be noted that the following is for illustration only and is not intended to limit the present invention. Generally speaking, unless there is a single-well-defined well-localised-symptom most treatment regimens should start with a "general zone treatment", and such general zone treatment should form part of any treatment programme. FIG. 2 shows a general zone treatment, in this case spinal, also sometimes referred to as "three paths and six points". Other examples of such general zone treatments include treatment on the neck-and-shoulder-region, sometimes herein also referred to as "coathanger region", and the corresponding treatment as "coathanger treatment" or "coathanger method". In the following, all the described treatment regimens are performed using, by way of example, a handheld device as described in WO 2005/118061. Other devices may, however, also be used to provide the treatments described herein. Generally speaking, there are two ways of using such device, namely, firstly, putting the electrodes of the device in contact with the skin and sliding them over the skin whilst applying a plurality of electrons as a series of alternating current signals of a duration of approximately 5 to 100 µs and an initial amplitude of approximately 10V to 100V. This is also sometimes referred to as the "brushing technique".

In a second embodiment of the treatment regimens according to the present invention, the electrodes of the device are simply put in contact with the skin at indicated positions sequentially and the plurality of electrons is applied in a series of alternating current signals as defined above, whilst the electrodes are held stationary in each position. The skin biofeedback is measured and recorded, for example by measuring skin impedance and its rate of change. This is performed for a number of adjacent sites, and the site having the strongest biofeedback, such as highest rate of change of skin impedance or the site having a local greatest difference of skin impedance or the site having a skin impedance rate of change higher than adjacent sites, is treated further by applying further electrons in a further series of alternating current signals of the same initial duration and same initial amplitude, for a defined period from 30 s to 5 min and, optionally, until the skin impedance does not change anymore. This is also sometimes referred to as the "numerical technique", without such term necessarily implying a strictly quantitative approach being taken. For example, the user interface in this embodiment does not have to be numerical in a literal sense; it suffices if such user interface allows a qualitative comparison of skin impedances or of skin impedance rates of change at different sites.

A "site" in accordance with the present invention is an area of approximately 10-20 cm$^2$, preferably of a circular, square or rectangular shape, although other shapes are also possible.

At the end of any treatment, either the brushing technique or the numerical technique, a so-called frequency modulation may be performed wherein a series of alternating current signals is applied which are frequency modulated through a range of frequencies, e.g. from approximately 15 Hz to approximately 351 Hz, preferably over a period of approximately 5-15 s.

Figure 1:
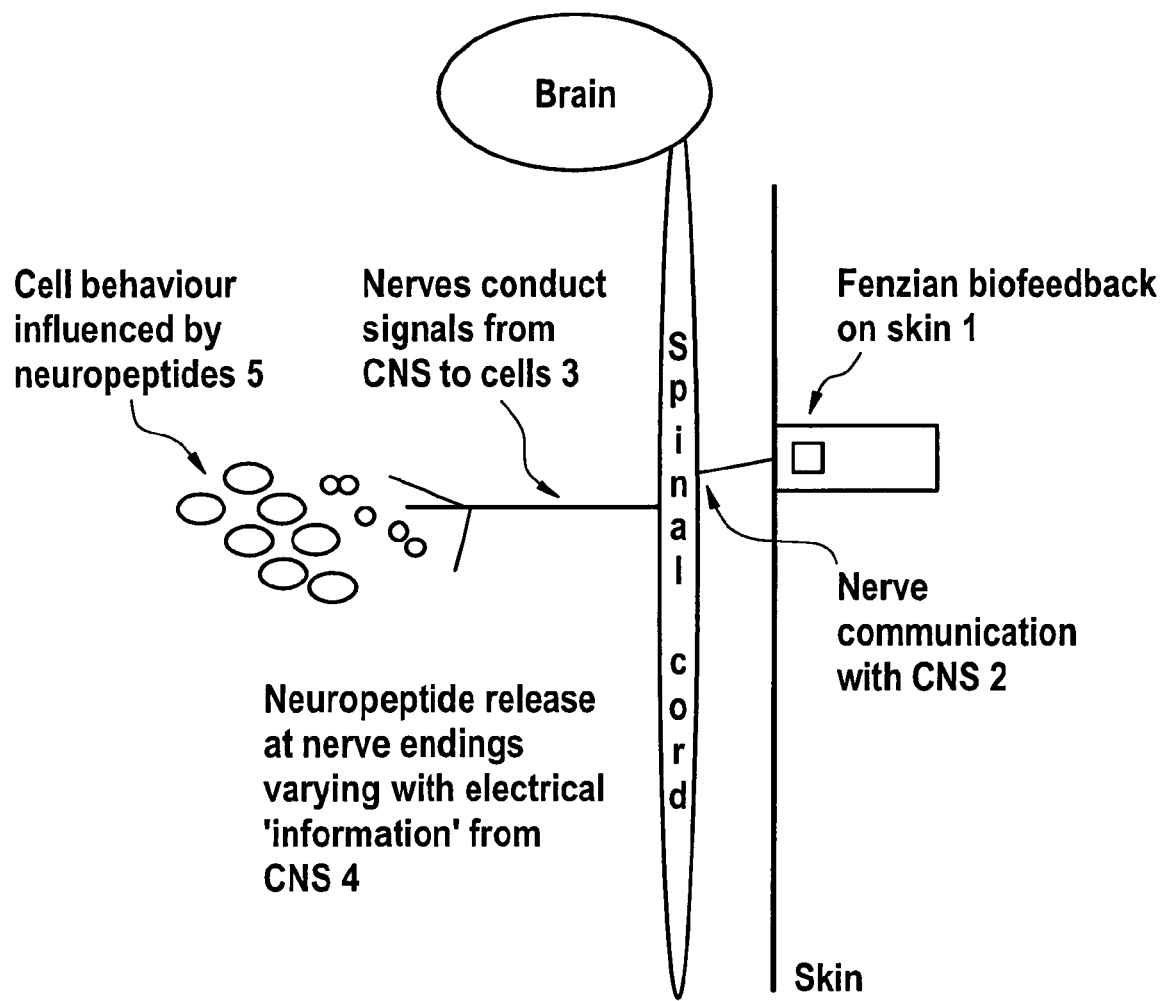
FIG. 1 is a schematic drawing of the putative mechanism underlying an embodiment of the present invention and the use of the electrons for treating diseases; the various stages of the putative mechanism underlying an embodiment of the present invention are denoted from "1" to "5,"
Figure 2A:
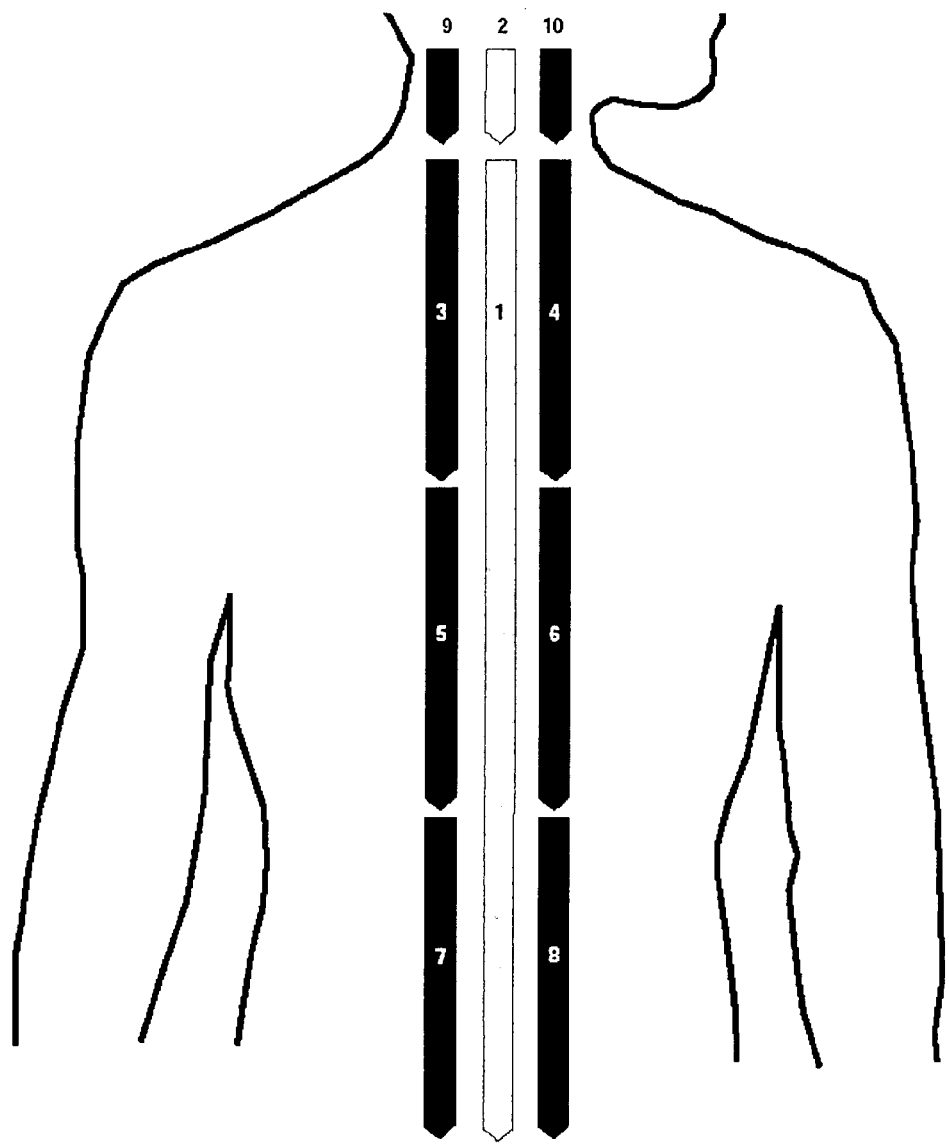
FIG. 2 shows the first stage (2a) and second stage (2b) of one approach to a general zone spinal treatment, according to an embodiment of the invention.

The first part of a general zone spinal treatment is shown in FIG. 2a, wherein arrows indicate the direction of the brushing movement that is performed with the device, and the numbers refer to the order in which such brushing movements with the handheld device are performed, whilst applying the series of alternating current signals. The second stage of this general zone treatment is shown in FIG. 2b, wherein, again, a device is brushed in the direction of the arrows staring at arrow 1 and finishing at arrow 6.

Figure 3:
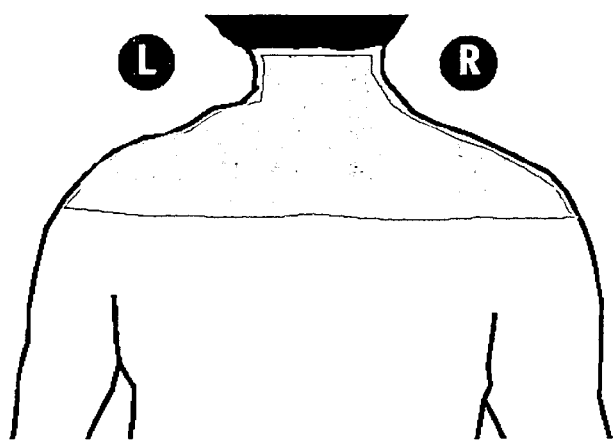
FIG. 3 shows a schematic representation of the treatment of the shoulder and neck region, herein also sometimes referred to as the "coathanger method general zone," according to an embodiment of the invention.

FIG. 3 shows a general scheme of another general zone treatment method, the so-called "coat hanger method", wherein the area of the shoulder and neck is treated. If a device is used as described in WO 2005/118061, this should typically be held in the orientation as indicated in FIG. 3 whilst brushing over the indicated area.

FIG. 4 shows an example of treatment areas for respiratory/chest problems, again, where a brushing movement is performed with the device over the areas indicated in the figure, typically including movement along the ribs and starting at the 12$^{th}$ rib and working upwards and alternating the sides.

Figure 5:
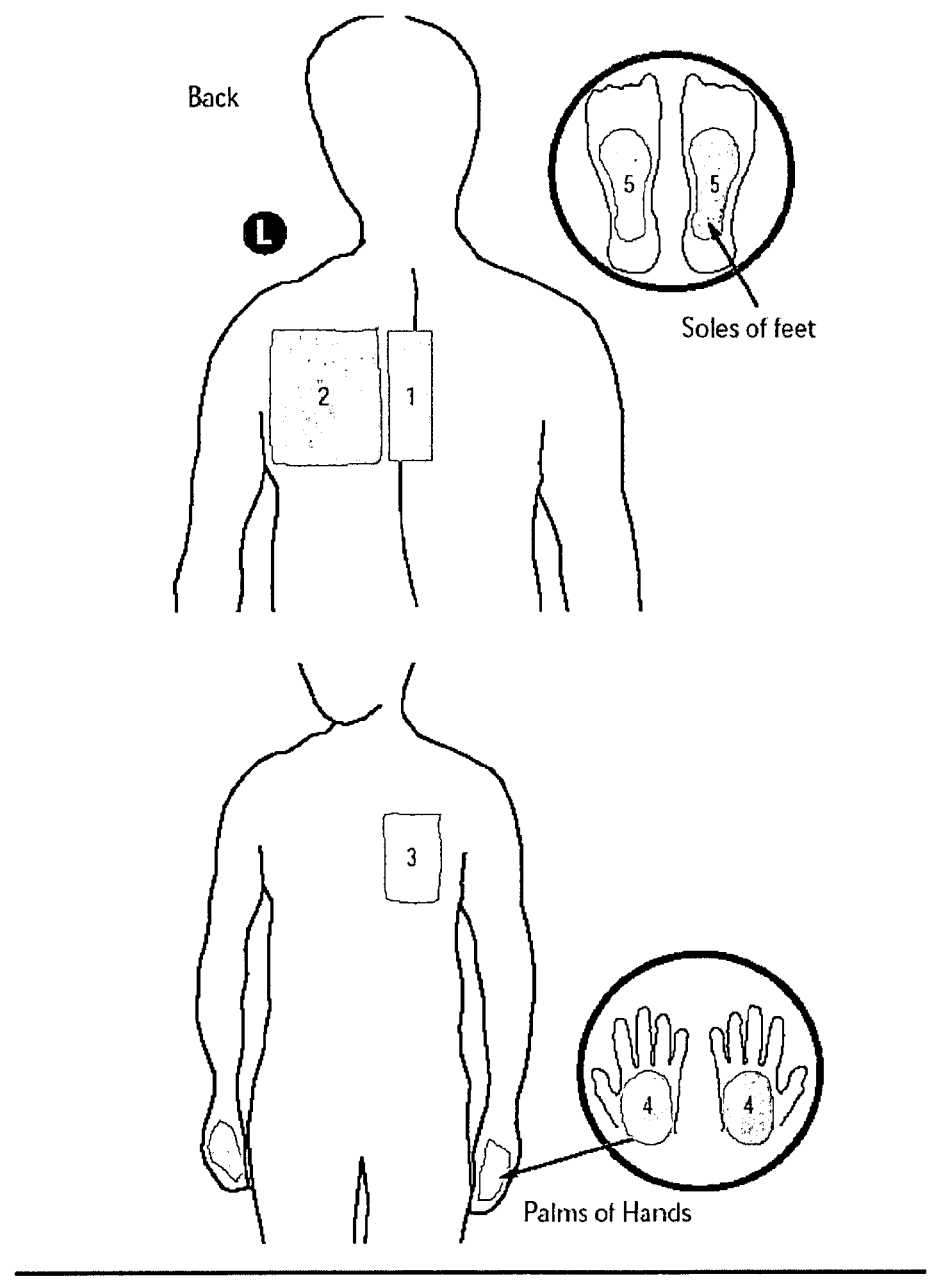
FIG. 5 shows a schematic representation of one example approach to the treatment areas for diseases of the cardiovascular system, according to an embodiment of the invention.

FIG. 5 shows an example of zones for treatment for diseases of the cardio vascular system, using a brushing approach.

Figure 7:
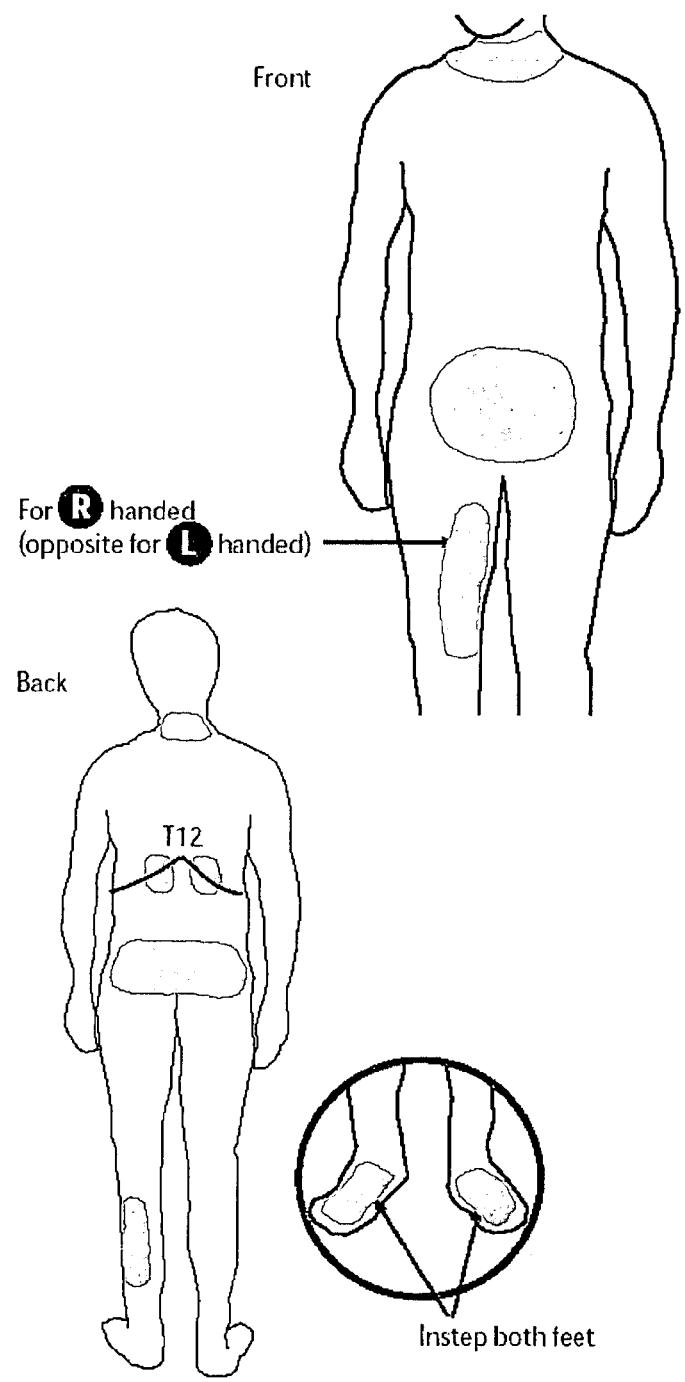
FIG. 7 shows a schematic representation of one example approach to the treatment areas for genito-urinary diseases, in particular pathological states in the pelvic region, according to an embodiment of the invention.

FIG. 6 shows an example of areas for treatment of diseases of the gastroenterological system, again using a brushing approach;

FIG. 7 shows an example of treatment areas for problems in the lower abdomen, in particular the pelvic region;

FIG. 8 shows an example of treatment areas for diseases/pathological states of the kidney/urinary tract; typically the kidney area is treated, and treatment is continued in one movement around to the front on both sides.

Figure 9A:
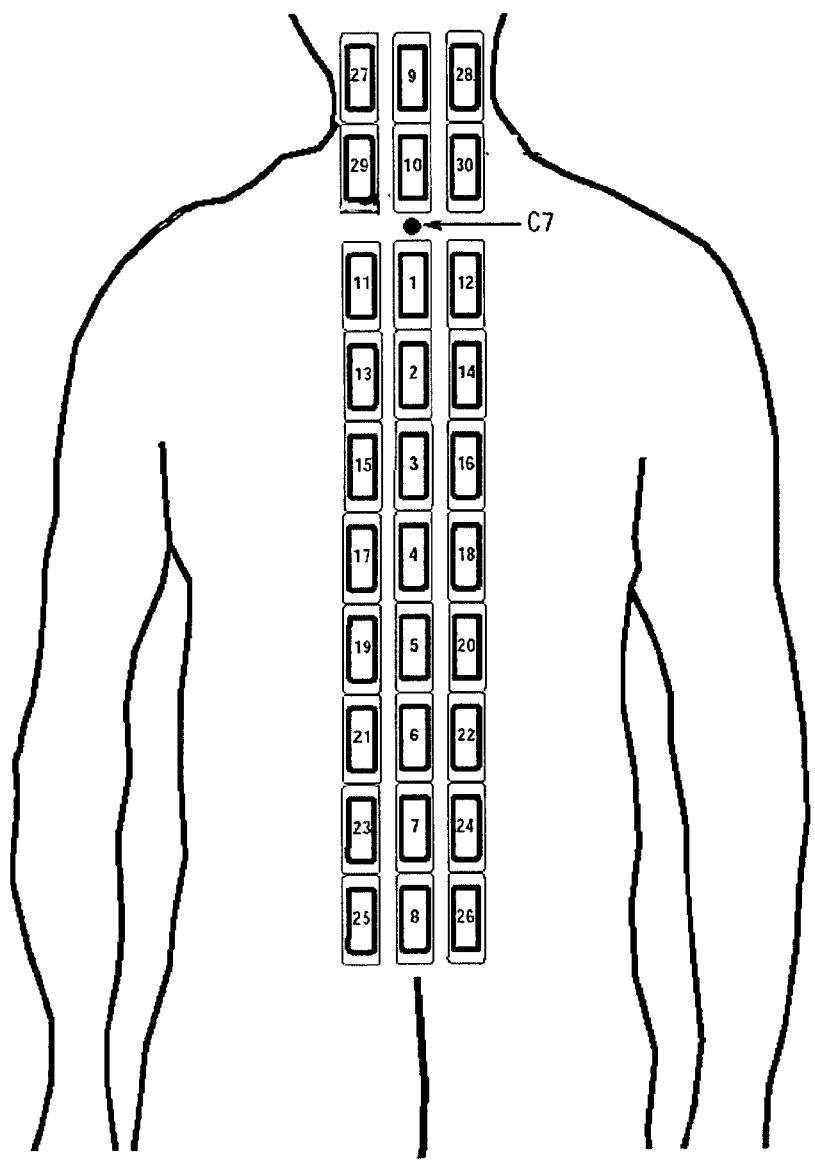

FIG. 9a shows an example of the first stage of a general zone treatment, in this case a spinal treatment, using the aforementioned numerical approach, wherein the device is held at numbered positions as indicated in the figure, and the skin impedance and the rate of change of skin impedance is measured, as described above. Those positions or sites appearing to have a local maximum of skin biofeedback in relation to adjacent sites are further treated by subsequent applications of AC signals, and the site with the highest initial skin biofeedback overall is treated further by further application of AC signals until there is no useful change in skin biofeedback recorded anymore. The first round of further application of AC signals to those positions having local maxima is also sometimes herein referred to as "test" or "dose", and the second round of further application of AC signals is herein also sometimes referred to as "zero". The testphase usually takes less than 1 minute, and the zero phase is performed until no change in useful skin biofeedback can be detected, as, for example, measured by the rate of change of skin impedance which rate approaches or equals zero. Such zero phase typically takes from 1 to 4 minutes. FIG. 9b shows the second stage of this general zone treatment in the face and at the back, centered on vertebra C7, and at the front, centered on the suprasternal notch.

Figure 10:
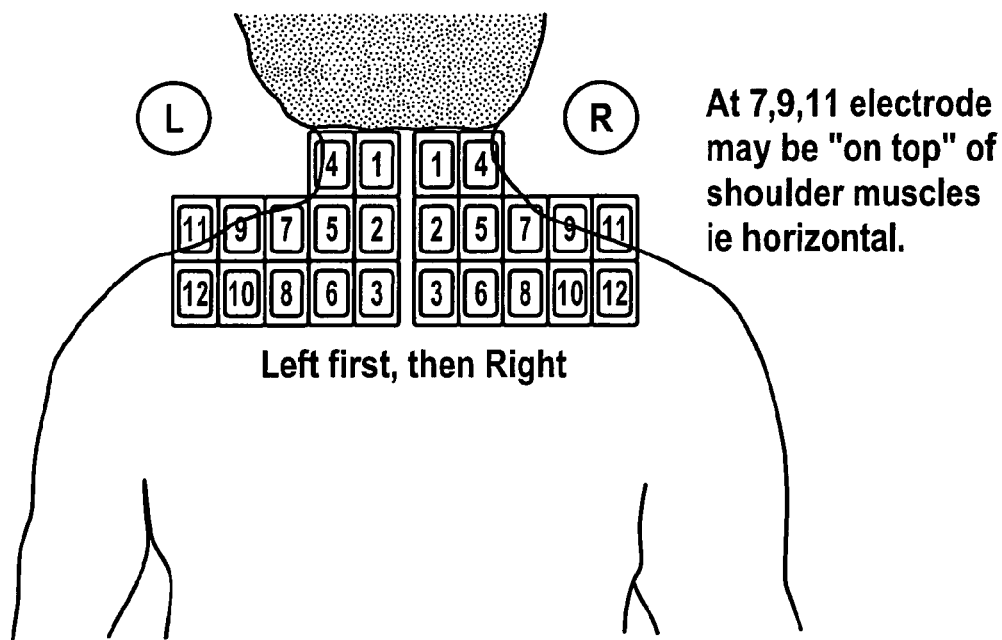
FIG. 10 shows another embodiment of one of the treatment methods based on the neck and shoulders (herein sometimes also referred to as the "coat hanger method general zone") using a numerical approach, according to an embodiment of the invention.

FIG. 10 shows another example of a general zone treatment, in this case focussing on the "coathanger" region, using a numerical approach.

FIG. 11 shows the positions for a numerical approach treatment at the forehead and the adrenal glands, wherein the numbered regions indicate the positions or sites, in which the plurality of electrons are to be applied as series of AC signals, and wherein positions or sites showing local maxima of skin impedance in comparison to surrounding sites or having the highest rate of change of skin impedance, are further treated ("tested") or "zeroed", i.e. until the skin biofeedback does not change usefully anymore, as, e.g. measured by the rate of change of skin impedance which approaches or equals zero FIG. 12 shows the various positions for a possible treatment of the lower abdomen/pelvic region, using the aforementioned numerical approach. At the front, the patient's hand, when placed on the abdomen with palmar crease along the vertical midline typically demarcates the area for treatment.

In the following, for a number of medical indications, some preferred treatment regions on the body are described. Unless specified otherwise, the term "treatment" refers to the application of a plurality of electrons as AC signals to one or more "sites" in the indicated body regions.

a) Diseases of the Respiratory System

For diseases of the respiratory system, treatment using a plurality of electrons applied as AC signals (in the following abbreviated as "treatment") could be applied to the back and the chest. More specifically, for asthma, pneumonia, respiratory allergy and bronchitis, treatment might focus on the thoracic region, in particular the thoracic spine and neck, the shoulders and the thorax. For asthma, treatment could include the suprasternal notch, the paravertebral lines in the thoracic spine and neck, the sternum, the vertebrae C7-C8. For rhinitis, sinusitis, trachiitis, pharyngitis, treatment might typically include the region over the nose, over the sinuses, over the front of neck and thoracic spine up to the neck. For otitis, treatment would probably include the region in front of and behind the ear, the line of the Eustachian tube and the neck. For pneumonia and bronchitis, the treatment should typically include regions over the lung areas.

b) Cardiovascular Diseases

For cardiovascular diseases, such as angina pectoris, ischaemic myocardial infarction, arrhythmia, post-myocardial infarction pain, myocarditis, heart failure and hypertension, treatment might be applied to the back and/or the chest of the patient in an area of the skin underneath of which the heart is located, and in an area of skin underneath of which the thoracic spine is located. Furthermore, the treatment could well include the palms of the hands and the soles of the feet of the patient, as shown in FIG. 5.

c) Gastroenterological Diseases

For gastroenterological diseases, electrons in the form of AC signals might be applied to the skin on the abdomen and/or in an area of skin underneath of which the affected organ or site is located. For example, for pathological states of the oesophagus, treatment could include regions of skin overlying the oesophagus and the liver. For stomach ulcers and gastritis, treatment could include an area of the skin overlying the liver, the sternum, the shins, as well as the neck and shoulders. For cirrhosis, treatment might typically include an area overlying the liver, the abdomen and the splenic area. For gallstones, treatment might include the area overlying the liver and the gallbladder. For pancreatitis, treatment should include the site of pain and the area overlying the pancreas. For constipation or diarrhoea, treatment might include the area overlying the liver and the colon. For rectal pathology, treatment could include the lower abdomen from the pubis to the umbilicus as well as the lower back, in particular the skin overlying the sacrum.

d) Skin Diseases

For skin diseases, treatment should focus on those regions of the skin which are affected by the skin disease, if such affected regions are not larger than approximately 10 cm$^2$ in total. If such affected area is larger, treatment might also focus on smaller healthy regions around the larger affected areas.

e) Musculo-Skeletal Diseases

Treatment should include regions overlying the affected element of the musculo-skeletal system, such as joint, bone, muscle or tendon. If the musculo-skeletal disease affects an extremity, the other, unaffected extremity should be treated in the same position as well.

f) Neurological Diseases

Figure 2B:
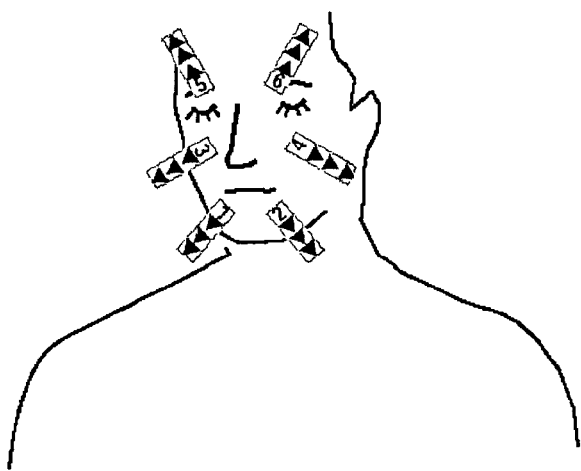

For neurological diseases, the treatment would include the back and/or chest and/or face and/or neck and/or skull and/or spine of the patient. If the neurological disease is a stroke, treatment should include the nearest available place on the skull to the site of injury, the back of the head, the neck, the area overlying the carotid artery and the six points on the face, as indicated in FIG. 2b. For trigeminal neuralgia, treatment should include the area over the trigeminal ganglion in front of the ear, the infra-orbital foramen, a region from the infra orbital zone back to the origin of the facial nerve and over the closed eyelids. For epilepsy, treatment might typically include the back, the neck and shoulders, the spine and the six points on the face as shown in FIG. 2b. For migraine, the treatment could include the area over the perceived site of pain, the spine, the neck and shoulders and the hands and feet, preferably the area that is typically covered by gloves and socks.

g) Ophthalmological Diseases

For ophthalmological diseases, treatment should include the periobital area, the neck, the six points of the face as shown in FIG. 2b and the area over the closed eyelids. For glaucoma, the treatment could include the area of the upper maxilla adjacent to the nose. For squints, treatment might include the area around and over the eye, especially laterally from the eye.

h) Genito-Urinary Diseases

For genito-urinary diseases, treatment should include the neck and shoulders and the area overlying the kidney, the bladder, the ureters, the liver, the pancreas and/or the spine. For male genital conditions, such as prostatism, impotence, infertility and testicular diseases, treatment would include areas of skin along the line of the ureters, the inguinal lymph nodes, the perineum, the scrotum, the penis, and/or the buttocks. For female genito-urinary diseases, treatment would include the abdomen and/or neck and/or lower back.

i) Inflammatory Diseases

For inflammatory diseases, treatment should include general approaches including the back, spine, face and chest, and also more local approaches focussing on the areas where symptoms of inflammation occur.

j) General Remarks

Generally, for any of the above-mentioned treatments, treatment should be performed in several sessions of applying electrons as AC signals, with each session typically lasting about 15 to 30 minutes. For acute pathological states, treatment should be in as many sessions as possible until the symptoms of the pathological state are relieved. For chronic pathological states, treatment may be in 1 to 10 sessions over the first two weeks, and may then be continued subject to revision by the practitioner.

Moreover, reference is now made to the following cases of patients which have undergone treatment using a plurality of electrons applied in accordance with the present invention which are given to illustrate, not to limit the present invention.

In the following example case studies, reference is made to the "Fenzian therapy" or "Fenzian treatment", which is herein meant to refer to the application of a plurality of electrons as a series of AC signals applied through an electron producing device, such as the one described in WO 2005/118061, in accordance with the present invention.

It should also be emphasized that all the following treatment protocols were performed in a confidential manner, and patients received such confidential treatment of an experimental nature. Confidential treatment was performed in the treating practitioner's medical practice or in the hospital.

Case 1:

The patient (female, born in 1929) initially presented in 1986 with a febrile illness, pneumonitis unresponsive to antibiotics and a migrating arthritis. At this point she had a butterfly erythematous rash on her face and the diagnosis of systemic lupus erythematosis (SLE) was made. At the time she responded to high dose steroids.

Over the past 17 years she has had recurrent episodes of SLE and has had every manifestation of the disease including poly-arthritis, pleurisy, pericarditis, nephritis, conjunctivitis. She suffered from episodes of severe anaemia and thromocytopaenia. She has averaged four hospital admissions per year as a result of symptoms of SLE or as a result of the complications of drug therapy.

Her drug regimen has included corticosteroids at varying doses since 1986 as the mainstay of treatment augmented at different times by a variety of non-steroidal anti-inflammatory drugs, azathioprine, plaquenil and methotrexate and ipratropium and fluticasone inhalers. In addition to the drugs to combat SLE she has been on medications to counteract the side effects of the steroids including omeprazole for gastrointestinal symptoms and fosamax for osteoporosis. In addition she was on calcium supplementation (Ideos) and multivitamins and minerals. She was on sertraline and citalopram to combat the depression associated with chronic illness.

She has suffered from complications associated with her therapy including a chronology of infections necessitating repeated courses of antibiotics (and regularly suffered from oral thrush as a result), symptoms of Cushing's (moon face, striae and acne), peptic ulceration and progressive osteoporosis. She has had a series of squamous cell carcinomas necessitating skin grafting and has bilateral cataracts which where removed. She had a perforated duodenal ulcer in 2003 necessitating 10 days on parenteral feeding in intensive care. Her condition was treated conservatively but developed a sinus from this ulcer to her uterus. Scans reveal a mass of adhesions in her abdomen. She has intermittent bouts of proteinuria and haematuria being attributed to her lupus and her drug therapy. At times during the course of this lady's illness it has been difficult to distinguish adverse drug effects from those of SLE or intercurrent disease. Steroid toxicity and Cushing's symptoms remits on reduction of the steroid dose but it has not been possible to withdraw steroids completely as the SLE would flair up.

The various manifestations of SLE and symptoms associated with adverse reactions to medication occurred sequentially but often several appeared together. Recurrent flair ups were often triggered by infections and acute periods often lasted for months. Remissions were never completely symptom free hence this patient had a progressively poorer and poorer quality of life.

In February 2004 this patient's medication included 30 mg corticosteroids/day, 25 mg Azathioprine/day, 7.5 mg methotrexate per week, 200 mg plaquenil/day. She was house bound and was suffering from polyarthralgia. She had no energy and was in constant discomfort, which prevented her from sleeping, compounding her symptoms of fatigue. Mentally she was drained and was on citalopram 20 mg per day. Her physicians had exhausted all the treatment options and all combinations and doses of available therapeutic agents had been tried.

In March 2004 she commenced Fenzian therapy using a mixture of approaches, typically at 60 Hz with the voltage being adjusted to suit the biofeedback and sensation for the patient. Treatments included brushing and numerical approaches; finishing with a frequency cycle to the most reactive biofeedback sites. The patient was initially sceptical of this approach considering it unconventional. Initially treatment was administered every second day to her back and directly over the inflamed joints. The treatment episodes lasted about 20 minutes commencing with brushing and then more focused administration of the therapy. She now receives a short treatment once every two weeks.

Once her treatment began, her scepticism rapidly disappeared when she observed her body's response. She has been gradually weaned off all her anti SLE medication and was no longer on azthioprine, plaquenil, or methotrexate. In the further course of the Fenzian treatment, i.e. after 3 weeks of Fenzian treatment 5 days a week, she was on only 5 mg of corticosteroids per day and the moon face of Cushing's has disappeared. She had not been on such a low level of steroids since 1986.

The improvement in her signs and symptoms had been matched by increased energy levels and a dramatic improvement in her quality of life. She had resumed driving her car and socialising with friends. She was no longer on citalopram.

At the end of Fenzian treatment, i.e. a treatment for 6 weeks in total (i.e. 5 days a week for the first three weeks, and 2 days a week for the second three weeks), the patient was off all medication.

Case 2 Neurology
AS Aged 13
Main Complaint: Right Hemiparesis
Medical History

This patient presented with a right hemiparesis which had arisen when he was three years old (ten years earlier). At that time he had a subarachnoid haemorrhage and lost use of his right arm and leg, as well as his speech. The speech returned but he learned to live with his disability.

At the time of him seeking Fenzian treatment he wore braces on his right arm and leg. His main declared problem at the time was a wound in the palm of his right hand where the flexural dominance, which was increasing with age, was forcing his fingers into the palm of his hand. So strong was the dominance that his fingernails could not be cut, exacerbating the problem.

Family History

He had no other past medical history of note. In his family history, his mother is asthmatic; his father well. A younger brother had mild absence moments. His 14 yr old sister is fine.

Systemic Questioning:

AS had no other systemic ailments.

On Examination:

He was a delightful and determined boy, in early puberty. His speech was slightly unclear due to the presence of major dental bracing. The right arm and leg were both weak. He held his right arm behind his back as he stated that he "was ashamed of it being so small and useless". His right hand was markedly atrophic; being approximately half the size of the left hand. The fingers were very firmly pressed into the palm in an open sore where tendon sheaths were clearly visible.

The family had been recommended both tendon severance and serial botox injections to ease the flexural dominance in his fingers. Both were being contemplated.

Treatment:

Fenzian treatment was begun on the first visit, and continued approximately weekly for the next two months. The early treatments included hand treatment and 'general' approaches along his spine and face. The treatments were matched to find the best approach for that day; varying with symptom and response, accordingly.

Outcome:

After three treatments his hand had relaxed enough for the nails to be cut. By the fifth treatment (two weeks into the course) the hole in the palm of his hand was healed. Over the next month of approximately weekly treatments, the right hand and arm had relaxed more and his parents noticed the hand falling more open whilst he was asleep. By the end of the first month he had discarded the right arm splint. The leg splint was retained for exercise only. By the end of the second month, the leg splint had been fully abandoned and AS was running without it. An unexpected finding was that his atrophic right hand had noticeably grown. It was approximately 1.5 cm longer than previously when measured from the palmar crease to the fingertips. Over the next six months, this process continued, as did his ability to open his hand. He was encouraged to use it more and some simple exercises were set.

Within 3 months of Fenzian treatment, he was able to compete in running races and to open his fingers, from time to time, at will.

A year after beginning treatment, he could open doors with his right hand and undertake other simple tasks with it. It had grown to within 5% of his other hand and his progress depended on his exercises. Four years after Fenzian treatment had begun, the previously hemiparetic boy with a hole in his atrophic hand began a college course in land management, and felt physically able to take part fully.

Case 3 Orthopaedic

JM is a 22 year old 'family support social worker'

She had a compound Monteggia fracture of her right (dominant) arm.

History:

JM had been completely well until a driver travelling towards her lost control and struck her car head-on.

After initial management and debridement of the wound, it was plated two days after the accident.

Over the next three months there was no evidence of callus or new bone formation and she was told to expect to retain the internal fixation for life.

In addition to the right arm injury, she had had a marked seatbelt 'burn' on her sternum, which remained tender.

Past Medical History/Family History:

There was nothing of note in her previous medical or family history. Both her sisters were fit and well. She lives with her boyfriend.

Medication

She was on analgesics to contain the pain.

On Examination:

She had a prominent surgical scar which had healed well. Hand movements were good, but with discomfort on wrist extension. She had apprehension and weakness on pronation and supination.

Four months after the accident, still with no bone growth she sought Fenzian treatment.

Treatment

She was treated over her sternum and her forearms on the first visit and felt faint for a short time during treatment. Subsequent treatments included treatment of her shoulders and neck as well as both forearms. The communication indicators of the Fenzian device quickly settled to a more 'normal' pattern.

Outcome:

The discomfort and apprehension rapidly settled by the third treatment (inside three weeks) and an X ray at three weeks showed 'significant bone growth'. She had only six treatments in all. The plate was removed three months after beginning Fenzian treatment and she had two treatments to assist the post-operative recovery. She remains well with full use of her arm, and has returned to work.

Case 4 Cardiac

CE is a property developer whose life was limited by angina.

History

CE had slowly developed angina over the previous three years when an angiogram confirmed three vessel coronary artery disease (including a 40% distal stenosis of the LAD). He was initially recommended angioplasty but this was revised to coronary artery bypass graft and measures to reduce his cholesterol level (from 8/9). At this time he would experience chest tightening after about 50 yards on level ground with marked worsening climbing stairs.

Past Medical History:

There was no related past medical or family history. He was not diabetic and only very occasionally had a cigar which he said he did not inhale. He was not hypertensive. He had previously had gout. No known allergies.

Family History:

His mother died at 86; father died at 59 of stomach cancer. He is married with two fit adult children.

Medication:

Atenolol 50 mg; Allopurinol 300 mg og. Lipitor 200 mg od.

On examination he looked well with normal heart rhythm and sounds. His blood pressure was 130/90. Distal pulses were normal.

Treatment:

First CE was sent for a second opinion to clarify his options. This led to a further recommendation for surgery.

Fenzian treatment was suggested as a prelude to surgery to render him fitter for the operation. Early Fenzian treatment was over the length of his back, as a general approach, and included treatments of his hands, neck, shoulders, and over his adrenal glands. After the first six treatments (which took two weeks) his chest tightening did not occur until after 200 yards walking and he "felt better". He decided to postpone the bypass and to continue Fenzian treatment. This lasted for 50 treatments over the course of a year, during which he was weaned off atenolol.

Outcome:

Ten years later he remains completely well and has had no angina.

Case 5 Asthma

SE is a an asthmatic labourer of 23 years old

History: 3 yrs earlier he had an asthmatic attack which he associated with a severe reaction to horses.

After this episode he became highly sensitive to horses, dust and alcohol. He had a regular cough producing white sputum.

Medication:

He was prescribed 2 courses of oral prednisolone during the 3 years but was maintained on becotide and salbutamol inhalers.

Even on his inhalers he could only manage to climb four or five stairs without stopping to regain his breath.

Past Medical History:

Wisdom teeth removed; tonsillectomy as a child; left $5^{th}$ toe straightened.

Family History:

Father angina; mother asthmatic; sister well.

Allergies:

Hay fever from grass. Sensitive to horses, dust and alcohol. Systemic questioning was unremarkable.

On Examination:

His breath sounds were wheezy.

Treatment:

Fenzian treatment was begun three times a week, treating his back, face and chest as the protocols led. He had some areas of high biofeedback activity on his face which settled as he was weaned off his inhalers over the first week. By the third week, he was off medication and asymptomatic. Treatment continued once a week for six weeks. He has remained free of asthma for the past five years and is not allergic to dust or alcohol. He has not tested his sensitivity to horses.

The only Fenzian treatment he has received since has related to injuries sustained whilst snowboarding or from heavy labour. He has remained off all medication.

Case 6 Gastrointestinal/Orthopaedic

GB was a 33 yr old highly skilled woodworker when he first presented for Fenzian treatment.

History:

He had a five year history of colicy abdominal pains with bleeding and disturbed bowel habit. A combination of colonoscopy and specialist opinion led to a diagnosis of Crohn's disease This was treated aggressively with oral steroids for five years which contained the symptoms.

He had associated right shoulder, bilateral hip and back pain which was initially attributed to the Crohn's. It was the neck and shoulder pain for which he sought treatment.

He had no other noted past medical history.

Family History:

Unknown

On systemic questioning he revealed a marked cough which was painful—"catching him in the back". He commented on some urinary urgency. He was unaware of any allergies and was generally careful with food and drank no alcohol.

Medication:

He was on 30 mg prednisolone od.

On examination he looked well with a normal pulse and blood pressure. His chest sounded clear. Most marked was general stiffness on neck movements, shoulder movements and hip movements (left worse than right). His abdomen was soft with normal sounds. Neck flexion to the left was worse than to the right. He described marked mid-thoracic tenderness and his left hip was limited in abduction, flexion and rotation; both internal and external.

Treatment:

He was initially treated along his spine from neck to coccyx with prominent activity with Fenzian being found in his neck and mid thorax. Immediately after the first Fenzian treatment he felt significant relief. The stiffness did return the next day. Over the next four weeks he was treated four days a week and he was weaned off his steroid medication. At this time his previous hip X-ray reports surfaced stating that he had "severe avascular necrosis of the left femoral head". The hip became much less painful and a new X-ray was reported as showing "mild avascular necrosis of the left femorL head". Fenzian treatment continued with less regularity to once a week, focussing more on his hips and abdomen as the biofeedback dictated. Another X-ray three months after Fenzian treatment had begun showed "no evidence of avascular necrosis". However, an orthopaedic surgeon, seeing him for a routine follow up decided that he thought there was an 'acetabular cyst'. Even though the patient was asymptomatic, with full hip movement, he decided to aspirate the cyst. Unfortunately, in doing so he disrupted the acetabulum. This was replaced—but the femoral head was seen to be normal.

Outcome:

The patient remained well after treatment was stopped after five months or approximately weekly visits.

However, two years later, he called to say that he was stiff and breathless, with painful breathing again, had had some blood tests and "felt rough". He received a Fenzian treatment on a Friday and the following Monday (by which time he was feeling well with full movement and painless breathing). The blood test results were sent to him with an accompanying letter which urgently recalled him for resumption of steroid treatment as he was found to have had an ESR of 62 and to be HLA B27 positive, implying a diagnosis of ankylosing spondylitis. He chose not to return to steroids and has remained well, with no discomfort or breathlessness for the past four years. His Crohn's disease symptoms also never resurfaced.

Case 7 Asthma/Osteoporosis

This patient complained of severe, debilitating neck pains.

History:

The neck pain had a gradual onset over three years to a level where she "took over sixteen small incremental movements to turn over in bed". Movements were extremely limited; in particular in rotation and anterior flexion.

Past Medical History:

She had had asthma for 27 years, most of it treated with either inhaled or oral steroids. Cholecystectomy/appendicectomy 25 years ago; Thyroid cyst 15 years ago; bladder repair 28 years ago. Left knee arthroscopy/washout 10 years ago.

Family History:

Her mother's side of the family has a strong link with allergies and eczemas. Her mother died at 73 of unknown cause. Her father is still alive at 87. She has a son and daughter who are both "wheezy". Her husband is well.

Medication:

She was on Flixotide 500 μg bd; Serevent 50 mg bd; Duovent 2 puffs qds; Ventolin 2 puffs prn.

She had no known allergies.

On Examination:

She looked well but stated that she felt profoundly depressed about her predicament. Her chest was clear apart from a mild mid-systolic murmur of mitral leaf prolapse with mild regurgitation. Her neck movements were very limited; both active and passive. She had marked apprehension about any passive movements. The remainder of her spinal movements were normal. She had no neurological deficit.

Treatment:

The approach was based on a premise that her neck osteoporosis was the result of prolonged steroid use for asthma. Treatment was aimed at weaning her off medication and stimulating bone growth in her neck.

Initial treatment included a 'coat hanger' general approach with focal treatments to her neck and face on subsequent visits as the biofeedback indicated. Her entire spinal length was treated every week, approximately using another 'general' technique. Within three weeks she was off all medication and no longer having any chest symptoms. The treatments to improve her bone growth continued approximately twice a week for four months and then reduced further to treat her if she felt discomfort. These treatments included treatment of neck, face arms and hands.

Outcome:

after three months her neck symptoms had improved markedly. After six months she was rarely troubled. Six years later she remains free of neck pain and asthma; being able to carry out any activity she chooses.

Case 8 Acute Sinusitis (Infection)

JH, an otherwise fit 26 year old farmer presented with acute bilateral maxillary sinusitis.

History:

The sinusitis had begun a week after his three-year-old son had developed a cold (it was the common sequence for him to develop sinusitis after his children had colds). The infection had not responded to antibiotics and he was in severe pain.

Past Medical History:

Apart from sinusitis, he had no past medical history or family history of note. He was married with two young children aged 3 and 4. He had no known allergies.

Medication:

He had finished a course of antibiotics and was on strong analgesia.

On Examination:

His face was swollen and red with inflammation. Both cheeks were tender and he had a partial ptosis of both eyes. There were some palpable lymph nodes behind his left ear.

Treatment:

Fenzian treatment was initiated over both maxillae; right, then left. Within five minutes he felt great relief from pain and after ten minutes of treatment he was pain free. A more general treatment of his shoulders was added the same afternoon, even though he remained pain-free. The following morning was still pain free; his face looked normal, and he felt much better. He had a general protocol treatment of his back and face. The following day he felt fine. In the four years since then, he had had no recurrence of sinusitis in spite of his children having had several colds.

While specific embodiments of the invention have been illustrated and described, it will be clear that the invention is not limited to these embodiments only. Numerous modifications, changes, variations, substitutions and equivalents will be apparent to those skilled in the art without departing from the spirit and scope of the invention as described in the claims. In general, in the following claims, the terms used should not be construed to limit the invention to the specific embodiments disclosed in the specification, but should be construed to include all systems and methods that operate under the claims set forth hereinbelow. Thus, it is intended that the invention covers the modifications and variations of this invention provided they come within the scope of the appended claims and their equivalents.

The features of the present invention disclosed in the specification, the claims and/or in the accompanying drawings, may, both separately and in any combination thereof, be material for realizing the invention in various forms thereof.

The invention claimed is:

1. A method for restoring a patient's health and for alleviating or curing Crohn's disease, wherein the method comprises:
applying a plurality of electrons to the body of a patient having a disease selected from diseases of the respiratory system, diseases of the cardiovascular system, diseases of the gastroenterological system, skin diseases, muscular-skeletal diseases, neurological diseases, ophthalmological diseases, genito-urinary diseases, and inflammatory diseases, wherein said plurality of electrons are applied, using a device having electrodes, as a series of alternating current (AC) signals of a duration of approximately 5 to 100 μs and an amplitude of approximately 10 V to 100 V, and wherein said AC signals are applied at a plurality of sites on the skin of the body of said patient by placing the electrodes of said device at said sites on the skin;
during the application of said AC signals, determining the impedance of said skin and the rate of change of said impedance at said sites;
selecting, from said sites, a site or a subset of sites having the highest rate of change of skin impedance, the highest skin impedance in comparison to other sites, and/or a skin impedance higher than adjacent sites; and
applying additional AC signals to said selected one site or said selected subset of sites.

2. The method according to claim 1, wherein said patient is a human patient.

3. The method according to claim 1, wherein said AC signals are applied at said plurality of sites by sliding the electrodes of said device over the skin at said sites, wherein the method further comprises:
monitoring changes in friction of the skin against said device, changes of sensation of the patient, changes in color of the skin, or a combination thereof;
during the application of said AC signals, selecting, from said sites, a site or a sub-set of sites exhibiting a change of friction of the skin against said device, a change of sensation of the patient, a change of color of the skin, or a combination thereof; and applying additional AC signals to said selected one site or said selected subset of sites.

4. The method according to claim 1, wherein at said selected one site or said selected subset of sites, applying additional AC signals for a period of time from 30 seconds to 5 minutes.

5. The method, according to claim 4, wherein at said selected one site or said selected subset of sites, additional AC signals are applied until the rate of change of skin impedance is zero.

* * * * *